US008518105B2

(12) United States Patent
Hossainy et al.

(10) Patent No.: US 8,518,105 B2
(45) Date of Patent: Aug. 27, 2013

(54) METHODS AND APPARATUSES FOR COATING A LESION

(75) Inventors: Syed Faiyaz Ahmed Hossainy, Fremont, CA (US); Mikael Trollsas, San Jose, CA (US); Thierry Glauser, Redwood City, CA (US); Yiwen Eveleen Tang, San Jose, CA (US); Eugene T. Michal, San Francisco, CA (US)

(73) Assignee: Abbott Cardiovascular System Inc., Santa Clara, CA (US)

( * ) Notice: Subject to any disclaimer, the term of this patent is extended or adjusted under 35 U.S.C. 154(b) by 608 days.

(21) Appl. No.: 11/726,647

(22) Filed: Mar. 21, 2007

(65) Prior Publication Data

US 2009/0005849 A1 Jan. 1, 2009

Related U.S. Application Data

(60) Provisional application No. 60/785,445, filed on Mar. 24, 2006.

(51) Int. Cl.
| | | |
|---|---|---|
| *A61F 2/06* | (2013.01) | |
| *A61K 38/00* | (2006.01) | |
| *C07K 2/00* | (2006.01) | |
| *C07K 4/00* | (2006.01) | |
| *C07K 5/00* | (2006.01) | |
| *C07K 14/00* | (2006.01) | |
| *C07K 16/00* | (2006.01) | |
| *C07K 17/00* | (2006.01) | |

(52) U.S. Cl.
USPC ............ 623/1.39; 530/300; 604/103.01; 623/1.42

(58) Field of Classification Search
None
See application file for complete search history.

(56) References Cited

U.S. PATENT DOCUMENTS

| 5,336,256 A * | 8/1994 | Urry ............................ 623/1.44 |
| 5,709,653 A * | 1/1998 | Leone ............................. 604/20 |
| 5,807,306 A * | 9/1998 | Shapland et al. ............... 604/21 |
| 6,329,190 B1 * | 12/2001 | Wickham et al. .......... 435/235.1 |
| 7,179,784 B2 * | 2/2007 | Zhang et al. ..................... 514/2 |
| 2003/0120338 A1 | 6/2003 | Chobotov et al. |

FOREIGN PATENT DOCUMENTS

| EP | 1422242 | | 5/2004 |
| WO | WO 9943271 | * | 9/1999 |
| WO | WO-2004091592 | | 10/2004 |

OTHER PUBLICATIONS

Barath et al. Infiltrator Angioplasty Balloon Catheter: A Device for Combined Angioplasty and Intramural Site-Specific Treatment. Catheterization and Cardiovascular Diagnosis, 1997. vol. 41, pp. 333-341.*

Amols et al. Intracoronary Radiation for Prevention of Restenosis: Dose Perturbations Caused by Stents. Circulation 1998. vol. 98, pp. 2024-2029.*
Lambert et al. Local drug delivery catheters: functional comparison of porous and microporous designs. Coronary Artery Disease, 1993, vol. 4, pp. 269-475.*
Abbott Cardiovascular Systems Inc., PCT International Preliminary Report on Patentability mailed Oct. 9, 2008; PCT/US2007/007343.
Abbott Cardiovascular Systems Inc., PCT Search Report and Written Opinion mailed Jun. 16, 2008; PCT/US2007/007343.
Wright, E. R. et al., "Self-assembly of block copolymers derived from elastin-mimetic polypeptide sequences", Advanced Drug Delivery Reviews, 54, (2002),1057-1073.
Chen, YM, et al., "Cultivation of endothelial cells on adhesive protein-free synthetic polymer gels", Biomaterials 26, (2005), 4588-4596.
Huang, L, et al., "Generation of synthetic elastin-mimetic small diameter fibers and fiber networks", Macromolecules, 33, (2000), 2989-2997.
Nagapudi, K, et al., "Photomediated solid-state cross-linking of an elastin-mimetic recombinant protein polymer", Macromolecules, 35, (2002), 1730-1737.
Nagapudi, K, et al., "Viscoelastic and mechanical behavior of recombinant protein elastomers", Biomaterials, 26, (2005), 4695-4706.
Nederberg, F, et al., "Phosphoryl choline introduces dual activity in biomimetic ionomers", J. Am Chem. Soc., 126, (2004), 15350-15351.
Shah, P, et al., "Effects of recombinant apolipoprotein A-I$_{Milano}$ on aortic atherosclerosis in apolipoprotein E-Deficient mice", American Heart Association, Inc., 97, (1998), 780-784.
Slepian, MJ, et al., "$\beta_3$-Integrins rather than $\beta_1$-Integrins dominate integrin-matrix interactions involved in postinjury smooth muscle cell migration", American Heart Association, Inc., 97, (1998), 1818-1827.
Takagi, J, "Structural basis for ligand recognition by RGD (Arg-Gly-Asp)-dependent integrins", Molecular Environment of Integrins, Biochemical Society Focused Meeting, (2004), 403-406.
Ueno, H, et al., "Local expression of C-type natriuretic peptide markedly suppresses neointimal formation in rat injured arteries through an autocrine/parachine loop", American Heart Association, Inc., 96, (1997), 2272-2279.

* cited by examiner

*Primary Examiner* — Marcela M Cordero Garcia
(74) *Attorney, Agent, or Firm* — Angela Augustus; Blakely Sokoloff Taylor & Zafman LLP

(57) ABSTRACT

A method and apparatus to treat regions of a vessel is described. A protein elastin-based polymer is released from the apparatus to coat the vessel lining as a primary therapy or an adjunct therapy with the delivery and deployment of a stent with or without drug coating. The protein elastin-based polymer may include a triblock structure having an elastin pentapeptide as the flanking block and a hydrophilic variant of the pentapeptide as the middle block. Both the flanking and middle blocks can be modified to change the structural and chemical properties of the polymer. In particular, the protein elastin based polymer is adapted to perform at least one of controlling release of a treatment agent, stimulating endothelial cell growth and stabilizing the vulnerable plaque to prevent rupture of the vulnerable plaque.

50 Claims, 13 Drawing Sheets

[Flanking Block – Middle Block – Flanking Block]$_m$ $$[A_x \quad - \quad B_y \quad - \quad A_x]_m$$

(E.g., [AAAA – BBBBB – AAAA]$_m$)

where: each A = amino acid, amino acid sequence, or monomer
each B = amino acid, amino acid sequence, or monomer Flanking Blocks are identical, but components within each Flanking Block do not have to be identical:

Ex. each A can be any one of:

– a monomer
– an amino acid
– an amino acid sequence

FIG. 3

A = Val – Pro – Gly – Val – Gly = VPGVG   [SEQ ID NO. 1]

B = Val – Pro – Gly – Lys – Gly = VPGLG   [SEQ ID NO. 2]

$[A_x - B_y - A_x]_m = [A_4BA_4]_m$ $\qquad\qquad\qquad = [(VPGVG)_4(VPGLG)(VPGVG)_4]_m$   [SEQ ID NO. 3]

FIG. 4A

B = A, where at least one amino acid in
each of the amino acid sequence is
replaced by a more hydrophibic amino
acid, such as:   lysine          (Lys)
                 arginine        (Arg)
                 glutamic acid   (Glu)
                 aspartic acid   (Asp)

E.g.,   B = VPG(Lys)G     [SEQ ID NO. 6]

E.g.,   B = VPGV(Arg)     [SEQ ID NO. 12]

E.g.,   B = (Glu)PGV(Asp) [SEQ ID NO. 14]

FIG. 4B

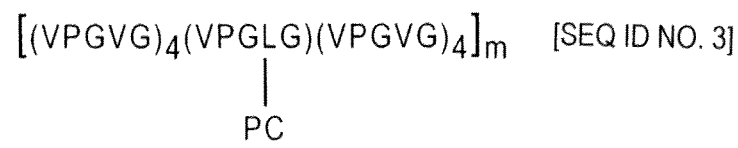
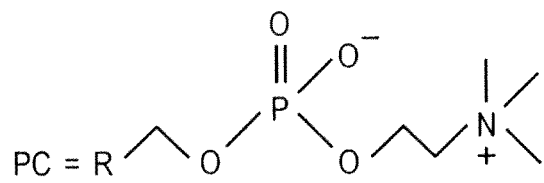
= Phosphoryl Choline
FIG. 5A
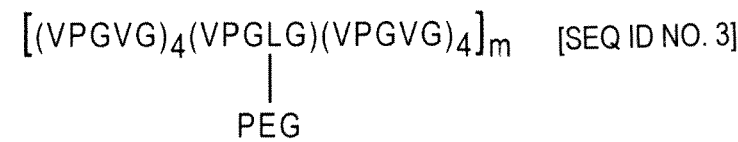
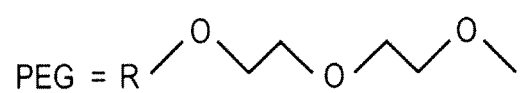
= Polyethylene Glycol
FIG. 5B

[(VPGVG)$_4$(VPGLG)(VPGVG)$_4$]$_m$  [SEQ ID NO. 3]
|
Acrylate

Acrylate = Any Acrylate Group

[(VPGVG)$_4$ X (VPGVG)$_4$]$_m$    [SEQ ID NOS. 4-5]

where X is the hydrophilic middle block
and can be any one of the following:

E.g., X = PEG =

E.g., X = Poly (Hydroxyethyl Methacrylate)

E.g., X = Poly (Vinyl Pyrolidinone)

E.g., X = Collagen

METHODS AND APPARATUSES FOR COATING A LESION

This application claims priority to U.S. Provisional Patent Application No. 60/785,445, filed on Mar. 24, 2006; this application claims the benefit of the provisional's filing date under 35 U.S.C. §119(e).

SEQUENCE LISTING

An electronic copy of the Sequence Listing entitled "5618P5104_SeqList_ST25" is incorporated herein by reference. This Sequence Listing consists of [SEQ ID NOS. 1-11].

FIELD OF THE INVENTION

The present invention relates generally to the treatment of vascular disease in regions of vessels, and more particularly, in one embodiment, to the stabilization of vulnerable plaque.

BACKGROUND OF THE INVENTION

Coronary heart disease is generally caused by the narrowing of coronary arteries by atherosclerosis, the buildup of fatty deposits in the lining of the arteries. The process that may lead to atherosclerosis begins with the accumulation of excess fats and cholesterol in the blood. These substances infiltrate and deposit in the lining of arteries, gradually increase in size to form deposits commonly referred to as plaque or atherosclerotic occlusions. Plaques narrow the arterial lumen and impede blood flow. Blood cells may collect around the plaque, eventually creating a blood clot that may block the artery completely.

"Vulnerable plaque" is different from typical occlusive plaques that impede blood flow. Where occlusive plaques line the vessel lumen and physically obstruct the flow of blood, vulnerable plaques are developed within the arterial wall. Since vulnerable plaques do not result in lumen narrowing, patients with vulnerable plaque are often symptom free as compared to patients with typical occlusive atherosclerotic plaque. Consequently, detection of vulnerable plaque in patients creates a new challenge for the treatment of heart disease in recent years because conventional methods for detecting heart disease, such as an angiogram, may not detect vulnerable plaque growth in the arterial wall. Before the development of various experimental modalities to detect vulnerable plaque, only an autopsy, after death, can reveal the plaque congested in arterial wall that could not have been detected or seen otherwise.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, but when combined with macrophage derived enzyme degradations, the fibrous cap can rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is termed "vulnerable" because of the unpredictable tendency of the plaque to rupture. It is thought that hemodynamic and cardiac forces, which yield circumferential stress, shear stress, and flexion stress, may cause disruption and contribute to mechanical rupture of the fibroatheroma type plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

FIG. 1A illustrates a section of a healthy artery 100 and FIG. 1B illustrates a cross-section of the same healthy artery 100. A healthy artery has a patent lumen 101. A monolayer of endothelial cells 102 covers the lining of the surface of the arterial lumen which is smooth and prevents blood clots. An artery is made of distinct layers. The internal elastic intima (IEL) 103 is an elastic layer just below the endothelial cells lining the arterial lumen. The media 104 consists mainly of muscle cells and extracellular matrix proteins and is located between the IEL and the external elastic lamina (EEL) 105. This muscular layer provides tone to the artery and controls the constriction and dilation of the artery. The EEL 105 separates the media from the adventitia 106. The adventitia is made of collagen and fibrous tissue and contains the vasa vasorum—which is a network of nerves, lymph vessels, and microarteries that supply oxygen, blood, and nutrients to the artery. When an artery is healthy, there is no or little atherosclerotic plaque deposited in the lumen and thus blood flows freely without obstruction and a person is symptom free of coronary disease.

FIG. 2A to 2C illustrate different views of a diseased artery with atherosclerotic occlusive plaque and a vulnerable plaque. As shown in a longitudinal section of the diseased artery in FIG. 2A, a narrowed arterial lumen 201 is caused by the presence of occlusive atherosclerosis. Atherosclerotic plaque 205 accumulates to impede and reduce blood flow through the arterial lumen and causes symptoms (e.g., angina pectoris). Narrowing of the arterial lumen is also shown in FIG. 2B which is taken at a cross-section AA of the FIG. 2A. The occlusive plaque deposits onto the lining of the artery and reduces the size of the arterial opening, thus limiting the cross-sectional area in which blood can flow through. In cases of typical coronary disease, besides the occlusive plaque that gathers along the lining of the artery, there are other changes that take place in the various layers of the arterial vasculature such as inflammation and increase in macrophages. Physical change in the artery is also observed. An enlargement of the artery, also known as positive remodeling, results from changes in the media and adventitia to enlarge the entire cross-section of the artery to adapt to the narrowing of the lumen by trying to allow the same amount of blood to flow through.

Also in FIG. 2A, downstream of the occlusive plaque 205, relative to the direction of blood flow 209, is a vulnerable plaque of the fibroatheroma type. The vulnerable plaque is represented by a fibrous cap 203 and a lipid core 202. Compared to an occlusive lesion which can easily be detected by an angiogram, the vulnerable plaque is much more difficult to detect. The lipid core 202 develops mostly within the arterial wall with minimal occlusive effects while the fibrous cap 203 surrounds and covers the lipid core 202, separating the lipid content of the core from the blood flow in the arterial lumen. As described above, in the presence of disease, the vessel responds with a "positive remodeling" phenomenon in attempt to maintain constant blood flow. In this case, the fibroatheroma vulnerable plaque has grown into the positively remodeled arterial wall limiting manifestations of vessel occlusion. FIG. 2C shows the vulnerable plaque in the cross-section BB of FIG. 2A. The lipid core 202 has grown into the intimal elastic lamina and merely shielding its thrombogenic contents from the blood stream by the fibrous cap 203.

Autopsy studies and other evidence strongly suggest that the presence of a current acute coronary syndrome (ACS) event and/or existing thrombus at certain plaque sites correlates to predicting a future ACS event in a given patient. The latter indicates the likelihood of a prior thrombotic event (e.g., fibroatheroma rupture) after which the plaque was able to heal itself, or complete occlusion of the vessel was somehow prevented. Autopsy studies also indicate that it is reasonable to expect that at least one vulnerable plaque could exist in each of the majority of catheterization laboratory patients being treated for arterial blockage from visible, occlusive atherosclerosis. Therefore, many of the patients at high risk for future ACS events may already be receiving interventional treatment. With the advancement of new diagnostic techniques, detection of vulnerable plaques is improving. Treating both the occlusive plaques and the vulnerable plaque in one procedure might be beneficial and desirable compared to separate treatments. The key to treat vulnerable plaque is to stabilize the vulnerable plaque and reduce the likelihood of rupture. Conventional stenting has been used to prevent plaque rupture. A more direct means of stabilizing the fibrous cap and thus the vulnerable plaque would provide a more reliable treatment.

SUMMARY OF THE INVENTION

Methods and apparatuses using a protein elastin-based polymer with an ability to deliver treatment agents to treat vessels, such as coronary arteries, are described. In one embodiment, a protein elastin-based polymer is released from a treatment agent delivery catheter to coat the vessel wall after delivery and deployment of a stent with or without a drug coating. The protein elastin-based polymer may be used to treat a variety of different regions which may be lesions, such as, a denuded endothelial region, a stenotic region treated or not treated for stenosis, a region anticipated to be stenotic, a potentially inflamed region as a precautionary measure and a vulnerable plaque. Such protein elastin-based polymer may include an "ABA" triblock structure having an elastin pentapeptide as the flanking blocks and a hydrophilic variant of the pentapeptide as the middle block. The elastic property of the polymer once coated onto the vessel wall helps to mechanically stabilize lesions or anticipated lesions on the vessel wall. The protein elastin based polymer can act as a protective coating and is also adapted to perform at least one of controlling release of a biologically or chemically active agent, stimulating endothelial cell growth and providing elasticity and mechanical strength to the vessel wall. A kit which includes the elastin-based polymer and a delivery system is also described.

BRIEF DESCRIPTION OF THE DRAWINGS

The present invention is illustrated by way of example, and not limitation, in the figures of the accompanying drawings in which:

FIG. 3 illustrates the general structure of the elastin mimetic protein.
FIG. 4A illustrates one embodiment of an "ABA" protein elastin triblock copolymer with a middle block consisting of VPGLG [SEQ ID NO. 1] and flanking blocks consisting of VPGVG [SEQ ID NO. 2].
FIG. 4B illustrates variations of a hydrophilic middle block retaining the β-spiral structure.
FIGS. 5A-5B illustrate two different variations of an "ABA" triblock structure $[(VPGVG)_4(VPGLG)_n(VPGVG)_4]_m$ [SEQ ID NO. 3].

DETAILED DESCRIPTION

Figure 1A:
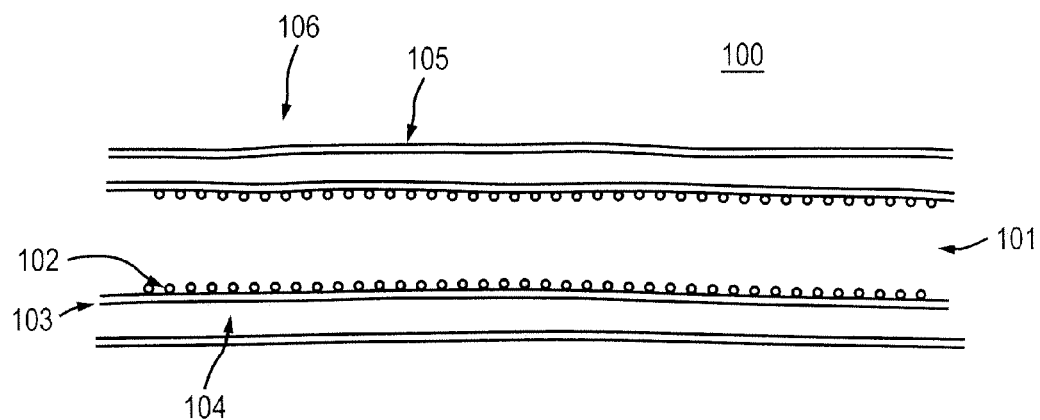
FIG. 1A illustrates a section of a healthy artery.
Figure 1B:
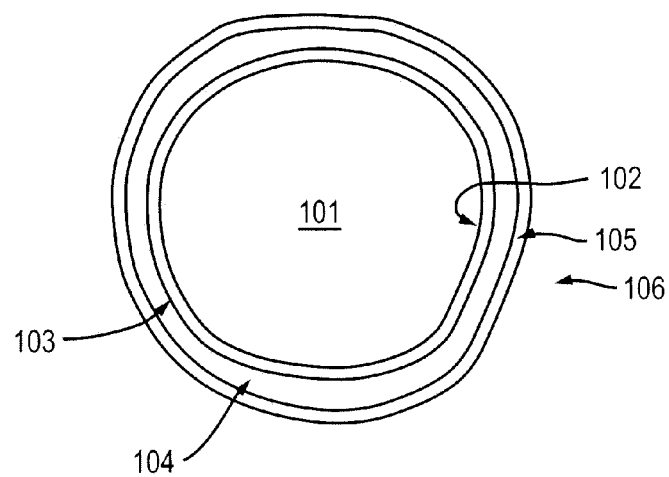
FIG. 1B illustrates a cross-section of a healthy arterial lumen.
Figure 2A:
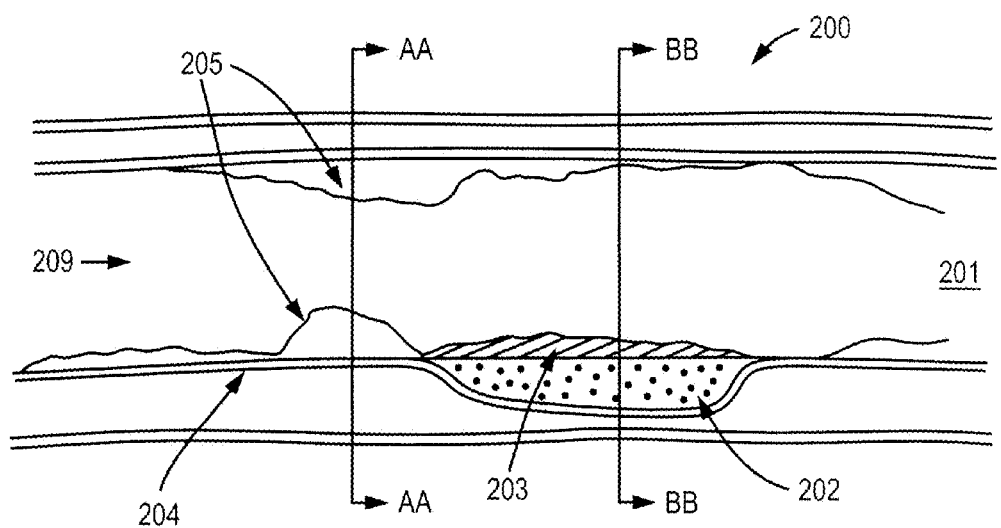
FIG. 2A illustrates a longitudinal section of a diseased artery.
Figure 2B:
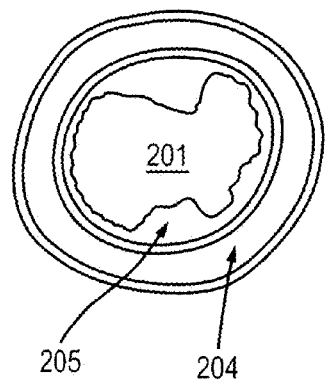
FIG. 2B illustrates the cross-section of a diseased arterial lumen with an occlusive plaque.
Figure 2C:
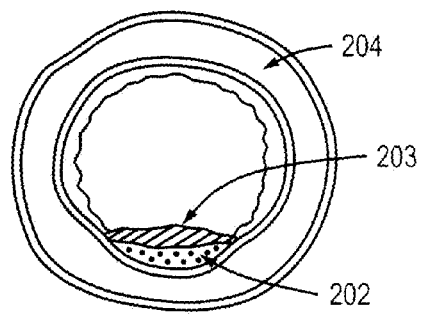
FIG. 2C illustrates the cross-section of a diseased arterial lumen with a vulnerable plaque.

In the following section, several embodiments of, for example, processes, compositions, devices and methods are described in order to thoroughly detail various embodiments. As would be understood by one skilled in the art, practicing the various embodiments of the present invention as described herein does not require the employment of all or even some of the specific details outlined herein. The term "treatment agent" is intended to include, but is not necessarily limited to, drugs, biologically active agents, chemically active agents, therapeutic agents, and the like, and pharmaceutical compositions thereof, which are used interchangeably to refer to agents (e.g., chemical or biological substances) to treat diseased regions of a blood vessel, such as in one embodiment, coronary artery and related diseases including for example, atherosclerotic occlusions and vulnerable plaque.

Apparatuses and their methods of use to treat different diseased regions of the vessel, including a denuded endothelial region, a stenotic region treated or not treated for stenosis, an inflamed region of a vessel, a region anticipated to be stenotic or inflammatory, and a vulnerable plaque are described. The coronary artery is just one of many vessels in the body where disease may form. Thus the apparatuses and methods to treat diseased regions of a vessel may be applied to any vessel of the body where stenosis, vulnerable plaque and other lesions, can be found. In one embodiment, a denuded endothelial region is coated with the protein elastin-based polymer to stimulate endothelial regrowth. In another embodiment, a stenotic region not treated for stenosis is coated with the protein elastin-based polymer to remove lipid from plaque and to break down plaque. In one embodiment a stenotic region treated for stenosis is coated with the protein elastin-based polymer to promote healing and re-endothelialization. In another embodiment an inflammatory region is coated with the protein elastin-based polymer containing anti-inflammatory drugs to reduce inflammation and to protect the region. In yet another embodiment, a region anticipated to be stenotic or potentially inflammatory is coated with the protein elastin-based polymer as a precautionary therapy to prevent stenosis or inflammation. Still, in another embodiment, the vulnerable plaque or the region of the artery containing the vulnerable plaque may be treated alone or in combination with a stent, wherein the stent may or may not be coated with a drug used to treat an occlusive atherosclerosis. Such drugs include, but are not intended to be limited to everolimus, sirolimus and paclitaxel. Treatment and stabilization of vulnerable plaque may also be applied without having to place a therapeutic implant (e.g., a stent) at the vulnerable plaque region.

Healthy arterial vessels are elastic and patent. Formation of atherosclerotic plaque contributes to lumen narrowing and leads to vascular changes thus reducing elasticity in the arterial walls. The artery responds by remodeling due to plaque accumulation. The direct coating of lesion with variations of protein polymers without stent implantation or as an adjunct therapy during stenting is disclosed. Traditional treatment of a discrete or diffused lesion may involve percutaneous transluminal procedures such as balloon angioplasty or stenting. These therapies involve mechanically inflating a balloon and/or expanding a stent. However, associated with these therapies are denudation of the endothelial cells and trauma to the vessel wall due to overstretching of the vessel. Consequently, through a cascade of events, the endothelial denudation, stretch injury and general vessel trauma lead to a healing response causing restenosis. Furthermore, besides physical stretch injury to the vessel, stenosis and inflammation may naturally develop due to accumulation of plaque or injury induced by long term hemodynamic effects created by high blood pressure and vessel geometry. Still, vulnerable plaque may develop in diseased vessels. In vulnerable plaque, reduced collagen content, degraded collagen, and thinning in the fibrous caps increase a plaque's vulnerability to rupture.

Thus, according to the present invention, coating the vessel wall provides an adjunctive or a primary therapy to treatment of diseased regions. In combination with stenting or angioplasty, whereby the paving or coating of protein elastin-based polymer increases healing response and promote endothelialization of the treated vessel region. Alternately, the protein elastin-based polymer can itself contain agents to remove lipid contents from the plaque or plaque dissolving agent to directly break down plaque, to provide a physical coating and mechanical support to the vessel wall. Still, as a precautionary measure, a protein elastin-based polymer can be used to coat the regions in a vessel to protect the region and prevent stenosis or inflammation because of intervention or unfavorable hemodynamics. Lastly, the protein elastin-based polymers can stabilize, reinforce/strengthen, and protect the fibrous cap of a vulnerable plaque in a vessel, thus reducing the likelihood of rupture.

Biomimetic materials have been used in tissue engineering. The arterial wall has been considered in general terms as a fiber-reinforced composite structure with associated mechanical properties largely a consequence of protein fiber networks. Elastin-mimetic protein is triblock polymer is one type of polymer suitable for this application. The polymer, its properties and its applications are described in "Viscoelastic and mechanical behavior of recombinant protein elastomers" by Nagapudi et al., Biomaterials 26 (2005) 4695-4706, which is incorporated by reference herein. In fact, arterial blood vessels can be viewed as a composition of elastin networks. Elastin fibers are structurally complex but provide the essential shape and energy recovery characteristics in the arterial wall. In an elastin network which may contain glycoproteins and glycosaminoglycans, the unique shape and energy recovery physical properties of network are attributed to elastin protein component such as tropoelastin. For example, elastin mimetic peptide polymers as applied in tissue engineering and the polymer's properties are described in, "Generation of Synthetic Elastin-Mimetic Small Diameter Fibers and Fiber Networks", by Huang, Macromolecules 2000, 33, 2989-2997, which is incorporated by reference herein.

In its native form, elastin is present as a network of elastic fibers that are cross-linked through available lysine residues found interspersed alanine-rich regions. Characteristically, cross-linking occurs in the solid state, after cellular secretion of tropoelastin with local fiber deposition, modulating the mechanical properties and enhancing the biostability of elastin. On the contrary, cross-linking of synthetic elastin-mimetic protein polymers have been performed in solution phase systems using gamma-irradiation, chemical and enzymatic-based reactions. Though such methods provide a measure of control over the degree of cross-linking, the chemical nature and the location of the cross-linking is often ill-defined, and such reaction schemes are inappropriate for heterogeneous multicomponent systems with a need to control the degree of cross-linking among individual constituents or to incorporate elements within the structure without adverse side-reactions. Such cross-linking properties of the elastin-mimetic protein polymer is described in, "Photomediated Solid-State Cross-Linking of an Elastin-Mimetic Recombinant Protein Polymer", by Nagapudi et al., Macromolecules 2002, 35, 1730-1737, which is incorporated as reference herein.

Recombinant DNA synthesis has been employed to produce elastin-mimetic protein triblock copolymers containing chemically distinct midblocks. For example, a repeating elastomeric peptide sequence of elastin, poly((Val-Pro-Gly-Val-Gly)$_4$(Val-Pro-Gly-Lys-Gly)(Val-Pro-Gly-Val-Gly)$_4$)$_{39}$ [SEQ ID NO. 3], of molecular weight 81 kDa, is obtained using genetic engeineering and microbial protein expression. Briefly, a concatameric gene of 3000 base pairs is isolated that encoded a repetitive polypeptide comprising 39 repeats of the elastin mimetic sequence. The protein polymer is expressed from recombinant plasmid pRAM1 in *E. coli* strain BLR (DE3) under isopropyl β-thiogalactropyranoside induction and purified to a high yield (64 mg/L) by reversible, temperature-induced precipitation from the cell lysate. Variation of the components in each block of the polymer structure contributes to a broad range of mechanical and viscoelastic responses ranging from plastic to elastic when expressed in different forms. The properties of the elastin-mimetic protein polymers can be modified and predictably altered based on polymer block size and structure.

Electrospinning technique has been proven to be a feasible method for creating protein elastin-based fibers from such protein polymers. In electrospinning, a polymer solution is subjected to an electric field that induces the accumulation of charge on the surface of a pendent drop. Mutual charge repulsion causes a force which directly opposes that produced by surface tension. At a critical value of electric field strength, a repulsive electric force exceeds the surface tension force, and a charged jet of solution is ejected. The jet develops into a series of fine filaments with a range of diameters that are characteristically on the order of tens or hundreds of nanometers. The range of properties exhibited by this class of protein triblock polymer allows for a variety of tissue engineering applications.

While the electrospinning technique is feasible, process parameters influences fiber morphology consequent of the solution viscosity, flow rate, electric field strength and the spinneret tip and the collecting surface in the electrospinning technique. In typical electrospinning, 2,2,2 Trifluoroethanol (TFE) and water are chosen as solvents. TFE is a good solvent for both the hydrophobic and hydrophilic blocks of these proteins at room temperature as compared to water which preferentially solvates the hydrophilic midblock. Using TFE and water can have the potential to exhibit different morphologies and mechanical properties. Protein polymer solutions (between about 1 and about 50 wt % and preferably between about 1 and about 30 wt %) are prepared in water or TFE. TFE based solutions are extruded with the aid of a syringe pump through a positively charged metal blunt tipped needle (e.g., 22 G×1.5 in) at ambient temperature and pressure and at a defined flow rate of about 0 µL/min to about 100 µL/min and preferably at about 30 to about 50 µL/min. Fibers are collected on a grounded aluminum plate located about 10 cm to about 20 cm from the needle tip with a preferred range of between about 13 to about 17 cm. A high voltage low current power supply is used to establish an electric potential gradient between about 0 and about 50 kV and preferably between about 0 kV and about 30 kV. In case of a water based system, for example, a peptide polymer solution between about 1 and about 30 wt % and preferably between about 5 and about 20 wt % is prepared in ultrafiltered grade, distilled, deionized water by mixing for about 12 hrs within the range of about 2° C. and about 8° C. and preferably between about 3° C. and about 6° C. and most preferably at about 4° C. Spinning is performed within the range of about 1° C. to about 12° C. and preferably at about 2° C. to about 6° C. with the polymer fibers emerging into a heated box at ambient pressure and heated to about 15° C. to about 30° C., preferably in the range of about 20° C. to about 25° C., and most preferably at between about 21° C. and about 24° C. The grounded aluminum plate is located inside a heated box because the aqueous polymer solution exhibit gel points between about 5° C. and about 18° C. and likely between about 8° C. and about 15° C.

Fiber morphology has been show to be influenced by the distance between the spinneret tip and the collecting plate, solution concentration, and flow rate. A distance of about 15 cm or within the range of about 13 and about 17 cm is determined to be an optimal distance for fiber formation. Fiber diameters ranging from about 300 nm to about 400 nm with an average width between 1.0 µm and 2.0 µm and likely about 1.5 µm can be observed in solution concentrations of about 10 wt % corresponding to solution viscosities greater than about 25 cP. At a flow rate of about 100 µL/min, approximately 1500 m of thin filament can be produced per minute. Morphology changes at solution concentrations of about 15 to about 20 wt % where flattened or ribbon-shaped fibers appear twisted during the spinning and deposition process. Ribbon shaped fibers are formed with diameters ranging from about 250 and about 600 nm can be observed from about a 20 wt % solution with an average fiber width of about 3.0 µm at low flow rates.

Naturally occurring elastomeric proteins can be found in a diverse range of animal species and tissues where they have evolved into precise structures to perform specific functions. These proteins exhibit rubber-like elasticity, undergo high deformation without rupture, stores energy in deformation, and recovers to their original state when stress is removed. The unique ability of these proteins to exhibit rubber-like elasticity relates to their primary and secondary structure as well as to those features such as protein self-assembly and other intermolecular interactions that dictate the formation of true or virtual networks. All elastomeric or elastin mimetic proteins can respond quickly to an applied force, meaning the monomers in the elastomeric or elastin mimetic proteins, typically consisting of repetitive glycine-rich peptide motifs, are flexible and conformationally free. Further, elastomeric macromolecules are cross-linked to form a network. Such elastic proteins combine their highly mobile domains with domains that form covalent or noncovalent cross-links. Thus, the size and properties of the mobile domains and degree of cross-linking can influence the elastic behavior of protein based materials.

When applied in the context of different diseased regions in the vessel, this triblock elastin pentapeptide is required to be processed into fibers and fabrics in which the protein polymer forms a cross-linked network. The coating thus formed on the vessel wall provides strength through its viscoelastic and stretch properties while different chemical compounds can attach to the polymer to either trap or store drug molecules or further chemically attach drug compounds or molecules to the polymer coating. Thus it is desirable to utilize a cross-linking strategy that is efficient in the solid state, achieves precise control over the nature and degree of cross-linking and facilitates spatial and temporal control over the reaction process. The elastin pentapeptide containing triblock can be electrospinned and woven into protein fibers as described above. The protein polymer is delivered in vivo via an aqueous solution below the lower critical solution temperature (LCST) of the polymer. When the solution is in contact with tissue at about 37° C., the polymer will result in a coating to coat the arterial wall and coat or pave over the various parts of the vessel such as a denuded endothelial region, a stenotic region treated or not treated for stenosis, a region anticipated to be stenotic or inflammatory, and a vulnerable plaque for treatment and/or reinforcement of the lesion and/or vessel. For instance, the polymer is typically delivered at about a 10% aqueous solution at about 4° C. into the tissue. Such a solution is typically delivered by a system or a catheter, preferably having an insulated wall, the ability to refrigerate, and/or maintain the solution at a temperature to prevent the solution from warming up and gelling inside the catheter because of the body temperature. For instance, the catheter can also be made from a thermoelectric material where conduction of electricity provides a cooling effect. Furthermore, short electrospun fibers can be added as reinforcement to the cross-linking or gelling of the polymer.

As such, an elastin-mimetic protein polymer can be produced with elastomeric and plastic-like properties in a manner similar to synthetic thermoplastic elastomers. FIG. 3 shows the general structure of the elastin-mimetic protein. In one embodiment, the elastin-based protein includes a sequence of an "ABA" triblock structure composed of elastin pentapeptide as the flanking block and a variant of the pentapeptide as the middle block. This sequence may be repeated but the triblock is represented by a middle block "B" and two flanking blocks "A". The polypeptide is synthesized by genetic engineering as discussed earlier. The flanking blocks provide the elastomeric properties of the protein and allow it to be stretched and elongated without rupture. The middle block is the back bone of the structure and its composition can be modified for special purposes such as drug delivery, increase cross-linking reaction, promote endothelialization, promote healing, breakdown of plaque and remove lipid from plaque, among other therapeutic possibilities, in treating atherosclerotic and vulnerable plaque in arteries such as the coronaries or other peripheral arteries in the body. This drug carrying and controlled releasing characteristic of the middle block provide unique attributes to the polymer, i.e., an ability to incorporate drugs and deliver them in a controlled manner. This characteristic contributes to the polymer's ability to promote endothelialization, to promote healing, to treat stenosis and inflammation, to remove lipid, and to break down plaque.

The flanking blocks and the middle block are generally similar to each other. Typically, each element or component within each flanking block can be an amino acid, an amino acid sequence, or a monomer. However, it is important to note that the various components or elements within each flanking block can be amino acid only, amino acid sequences only, monomers only, or any combination involving amino acids, amino acid sequences and monomers. Similarly, the middle block is formed by a number of components, just like the flanking blocks. Each component in the middle block can be an amino acid, an amino acid sequence, or a monomer. Also, the middle block can be made of amino acids only, amino acid sequences only, monomers only, or a combination involving amino acids, amino acid sequences and monomers. Furthermore, each flanking block and each middle block can have any number of components. The number of components in the flanking blocks can be the same or different as that in the middle block, while the ratio of flanking blocks to middle block(s) is arbitrary. The ratio can be varied based on the chemical and mechanical properties desired in the protein polymer such as coacervation properties and viscoelastic properties.

One unique characteristic of the elastin based protein polymer is its biocompatible property and flexibility for modification. The flanking blocks are responsible for the elastic properties of the protein which allows it to stretch, store energy and elongate. The middle block can take on the same chemical composition of the flanking block. However, the composition is often modified so that the molecule can alter some of its inherent chemical properties such as increasing efficiency in cross-linking reaction, changing the critical temperature of the protein polymer in solution, or changing mechanical properties such as viscoelastic and rheological properties. Furthermore, attaching other molecules or compound to the middle block or replacing the monomer, amino acid, amino acid sequence, or the combination with a different compound can incorporate other beneficial properties. For example, some changes can increase biocompatibility in vivo, or increase affinity to a particular cell, thus promote healing and endothelialization. In other cases, drug and drug carrying molecules for controlled release and delivery can be incorporated.

FIG. 4A shows one embodiment of a protein triblock copolymer with a middle block consisting of VPGLG (valine-proline-glycine-lysine-glycine) [SEQ ID NO. 1] and flanking blocks consisting of VPGVG (valine-proline glycine-valine-glycine) [SEQ ID NO. 2]. This protein triblock copolymer can also be expressed in the general form of $(VPGVG)_4 (VPGXG)_n (VPGVG)_4$ [SEQ ID NO. 6] where X=lysine. In this particular arrangement the middle block has the same composition as the flanking block except where the valine is replaced by lysine. The lysine substitution allows the protein to preserve its cross-linking reaction efficiency while contributing to the hydrophilicity of the protein. The central P-G element of the repeating hydrophobic pentapeptide (VPGVG) [SEQ ID NO. 2] adopts a type II reverse turn structure, forming a flexible helix or "β-spiral" on tandem sequence repetition. A conformational rearrangement from a random coil to a β-spiral structure promotes both intra- and intermolecular hydrophobic interactions and underlies the elastomeric restoring force in elastin. This facilitates both hydrophobically mediated polypeptide folding and molecular self-assembly. The nonconservative amino acid substitution of lysine can be performed without disruption of the β-spiral structure, while the incorporation of lysine permits spatially controlled chemical enzymatic cross-linking. Note that lysine can be replaced by any one of a more hydrophilic amino acid such as arginine, glutamic acid, or aspartic acid, while maintaining the same effect. Moreover, FIG. 4B illustrates variations of a hydrophilic middle block retaining the β-spiral structure. The hydrophobicity of the molecule can be retained while incorporating hydrophilic amino acids in the mid-block to the extent that the unique hydrophobic interactions that contribute to the elastic restoring properties are maintained.

As described above, this protein triblock polymer is delivered into the artery in an aqueous solution form in order to coat the artery. While the protein triblock polymer can be altered via its chemical composition to control its phase changing properties, the particular sequence described above naturally exists in a gel form at 37° C. Consequently, the protein triblock polymer will need to be delivered into the vessel at a temperature much lower than at body temperature of 37° C. It is believed that delivering the aqueous solution at about 1° C. to about 30° C. and preferably between the range of about 1° C. to about 10° C. will be suitable for most triblock protein polymer used for coating a region in a diseased vessel. A further benefit of delivering the aqueous solution at this low temperature is to achieve a cooling effect of the vessel which for example, may have a by-product therapeutic effect such as stabilizing the vulnerable plaque that tends to have a slightly higher temperature relative to the rest of the portions of an artery. For this particular embodiment, the triblock protein polymer can be delivered in situ in about 10% aqueous solution of the polymer at about 1° C. to about 10° C. and preferably between about 2° C. to about 6° C. Once the aqueous solution is in contact and coated over the vessel wall, as the temperature of the coating or the solution increases past the lower critical solution temperature of the polymer in aqueous form, gelation occurs and the polymer forms a gel or thin film coating to pave the vessel wall. As described earlier, a system or catheter delivering the polymer is made of an insulated material or a thermoelectric material that can keep the polymer cool while in the body to prevent gelation.

The biomimicry effect of this protein polymer coating and the chemical structure contributing to its elastic and biocompatible characteristics makes it a good candidate both as a stand alone and an adjunct therapy. This method of coating the vessel can be applied to protect a denuded endothelial region while promoting endothelial growth, to protect a potentially stenotic or inflammatory area due to unfavorable hemodynamics or plaque accumulation, to stabilize vulnerable plaque lesions, or to function as a primary therapy in stenotic regions to remove lipid from plaque or directly break down plaque in a vessel, as well as administered as a supplemental/adjunctive therapy to promote healing and endothelialization after angioplasty, stenting, or other interventions. The flexibility and ability to incorporate different molecules and drugs provide a wide range of therapeutic possibilities.

FIG. 5A and FIG. 5B show variations of the triblock structure [(VPGVG)$_4$(VPGLG)$_n$(VPGVG)$_4$]$_m$ [SEQ ID NO. 3]. As described above, pendant groups can be attached to at least one component such as amino acid, amino acid sequence or monomer to modify the properties of the protein. FIG. 5A shows one variation of the hydrophilic variant of the pentapeptide middle block having phosphorylcholine (PC) as a pendant group conjugated to the lysine amino acid in the middle block component. Similarly, FIG. 5B shows another variation of the hydrophilic variant of the pentapeptide middle block where polyethylene glycol (PEG) is conjugated to the lysine amino acid in the middle block component. PC and PEG are known to be "friendly" compounds to the native artery and possess non-fouling properties. For example, both PC and PEG have been known to use as coatings on implants such as stents to promote biocompatibility in the arterial environment. In addition PC's elastomeric properties can be tailored by controlling the phase separation between the zwitterions and the hydrophobic part of the copolymer. A description of the Phosphoryl Choline properties is provided in, "Phosphoryl Choline Introduces Dual Activity in Biomimetic Ionomers", J. Am. Chem. Soc. 2004 126 15350-15351. Crosslinked PEG has demonstrated exceptional elastomeric properties that can be adjusted by modifying the crosslink density, as disclosed in U.S. Patent Application No. U.S. 2003/0120338, titled "Advanced Endovascular Graft" by Chobotkov et al, which is hereby incorporated as reference A pentapeptide protein polymer coating with PC and PEG can also mechanically reinforce the fibrous cap to prevent rupture of vulnerable plaque. This polymer configuration can potentially lead to increase reendothelialization of the vessel lining. Increasing re-endothelialization can reduce the likelihood of thrombotic events and to promote healing, especially if the elastin-based protein is deposited or coated over the artery wall after a percutaneous intervention such as angioplasty, stenting or other procedure incurs injury and trauma to the vessel. Furthermore, this polymer is suitable as a preventative therapy in regions where stenosis or inflammation is anticipated as a result of unfavorable hemodynamic effects or plaque accumulation. Therefore, incorporation of PC and PEG provides an additional benefit of maximizing cell compatibility of the coating in interacting with endothelial cells and thus potentially improve healing response. As with the embodiment describe above without the pendant groups PC or PEG attached to the lysine amino acid in the component of the middle block, the triblock protein polymer with PC or PEG can be delivered into the artery in about a 10% aqueous solution at about 1° C. to about 10° C. and preferably between about 3° C. to about 6° C., below the lower critical solution temperature, such that the polymer can gel as it warms up after contact on the arterial wall. As described earlier, a system or catheter delivering the polymer is made of an insulated material or a thermoelectric material that can keep the polymer cool while in the body to prevent gelation.

Alternatively, instead of attaching PC and PEG to the fourth amino acid position of the middle block component amino acid sequence, different pro-healing compounds can be conjugated as pendant groups. For example, pro-healing compounds include, but are not intended to be limited to substances with pendant acid groups such as the amino acids glutamic acid, aspartic acid which are used to promote healing response. Other particularly effective pendant acidic groups would be sulfonic acids and salts of these acids (sulfonates). A description of the effects of such groups is provided in "Cultivation of endothelial cells on adhesive protein-free synthetic polymer gels", by Chen et al, Biomaterials, 26 (2005) 4588-4596. Besides attaching to the fourth position of the amino acid sequence in the middle block component, the groups mentioned above, PC, PEG, carboxylic acid, glutamic acid, aspartic acid, and sulfonates can also be attached to a different position, or in other words, replacing any other amino acids of the sequence, and still accomplishing the same effect. In addition, other charged moieties of polymers, such as pendant amines and amides are also known to have pro-healing effects and as result control the degree of endothelial cell adhesion. Thus this embodiment of the polymer is suitable for both adjunctive or primary treatment of a diseased region of the vessel, particularly in the treatment of denuded vessel regions or injured vessels.

Figure 5C:
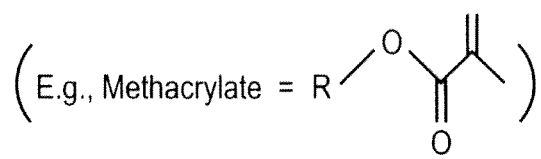
FIG. 5C illustrates a triblock structure $[(VPGVG)_4(VPGLG)_n(VPGVG)_4]_m$ [SEQ ID NO. 3] with an acrylate group conjugated to the lysine in the middle block.

Yet another variation of the triblock structure [(VPGVG)$_4$(VPGLG)$_n$(VPGVG)$_4$]$_m$ [SEQ ID NO. 3] is described in FIG. 5C. FIG. 5C shows a triblock structure [(VPGVG)$_4$(VPGLG)$_n$(VPGVG)$_4$]$_m$ [SEQ ID NO. 3] with an acrylate group conjugated to the lysine in the middle block. Elastomeric proteins modified with such groups as acrylates, are associated with lower inverse transition temperatures than the unmodified recombinant protein. Inverse transition temperature controls the temperature for fiber formation. Acrylate modified elastomeric proteins, AME proteins, with lower inverse transition temperature are known to exhibit better controlled fiber formation at room temperature; thus, the attached groups contribute for example to improved processing of the protein polymer. Furthermore, increased control of fiber formation leads to a viable route for solid-state cross-linking of the elastin-mimetic protein polymer. Besides advantages in processing and in promoting formation of a cross-linked network, an acrylate group also provides a different manner in which to deliver the protein polymer into the artery. For instance, the structure as shown in FIG. 5C with an acrylate group, conjugated to the lysine amino acid in the middle block component, can be delivered as a two component solution. A first component of the solution will be about a 10% to about 20% aqueous solution of the protein polymer, while the second component of the solution will be a di- or poly-thiol functionalized compound. Delivery and coating formation is accomplished by sequential, substantially simultaneous injection, and preferably simultaneous, of both components into the artery. Upon mixing in situ, the acrylates in the first solution will react upon mixing with the thiols to result in a cross-link material which coats the arterial wall and lesion, with or without a stent. This variation provides an alternate means of delivery without lowering the temperature of the aqueous solution of the polymer protein while increasing the strength of the resulting coating by enhancing the cross-linking network property while maintaining the natural biomimicry effect of the protein polymer. Alternate groups to the acrylate include, but are not intended to be limited to vinyl sulfones, maleiimids and activated esters. This embodiment provides strength, stability and protection and is suitable for treatment of vulnerable plaque and regions where protection is needed.

Figure 6:
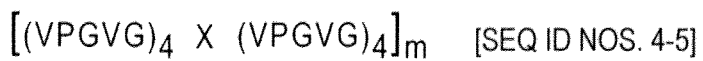
FIG. 6 illustrates an embodiment of a triblock protein polymer with a structure of $[(VPGVG)_4(X)_n(VPGVG)_4]_m$ [SEQ ID NOs. 4-5].

FIG. 6 illustrate yet another embodiment of a triblock protein polymer with a structure of $[(VPGVG)_4(X)_n(VPGVG)_4]_m$ [SEQ ID NOS. 4-5]. In this triblock structure, X is used as a middle block, replacing (VPGLG) [SEQ ID NO. 1] in the previous embodiments. A number of variations for X are possible in this embodiment. X can represent at least one of the following: polyethelene glycol (PEG), poly(hydroxyethyl methacrylate), poly(vinyl pyrrolidinone), and collagen. These compounds are suitable for anti-inflammatory, antithrombotic applications. For example, they can be used to treat regions that are anticipated to be stenotic or inflammatory and even stenotic and inflammatory regions.

In the first example of using PEG as a middle block. The PEG group when used as a middle block can provide advantageous chemical and mechanical improvements. For instance, the compound has improved solubility, lower manufacturing cost, accelerated degradation, higher swelling and decreased thrombogenicity. Using a PEG group in the middle block may promote phase separation which can be used to control the elastic modulus of the material. If the PEG is water soluble, its molecular weight should be such that it can be excreted by the kidneys. For example, a value of about 20 kDa is for common PEGs, but modification of this macromolecule can change this value. Moreover, it can be used as linkers for peptides. The polymer can be delivered at about 10 to about 20% aqueous solution of this polymer at a temperature lower than its lower critical solution temperature. The delivery temperature can be at about 1° C. to about 10° C. and preferably at about 2° C. to about 6° C. The lower temperature during delivery as described above can have a cooling effect on the artery and may help reduce local inflammation and stabilize any region or vulnerable plaque. Further, as the temperature of the polymer protein increases, gelation occurs and will coat the arterial wall and lesion, with or without a stent, with a thin film, gel or coat of the triblock protein polymer.

In another example, poly(hydroxyethyl methacrylate) is used as a middle block. Liken to the characteristics of using PEG as a middle block, using poly(hydroxyethyl methacrylate) (poly(HEMA)) as middle block also provide similar advantageous chemical and mechanical improvements. For instance, the compound has improved solubility, lower manufacturing cost, accelerated degradation of the protein polymer block, swelling and decreased thrombogenicity. Furthermore, the compound has an increased modulus and phase separation. If the poly(HEMA) is water soluble, its molecular weight should be such as it can be excreted by the kidneys. Further, it can be used as linkers for peptides.

In yet another example, poly(vinyl pyrrolidinone) can be used as a middle block. Liken to the characteristics of using PEG as a middle block, using poly(vinyl pyrrolidinone) as middle block also provide similar advantageous chemical and mechanical improvements. Just like PEG and poly(HEMA), the compound has improved solubility, lower manufacturing cost, accelerated degradation of the protein polymer block, swelling, and decreased thrombogenicity. Furthermore, the compound has an increased modulus and phase separation. If the poly(vinyl pyrrolidinone) is water soluble, its molecular weight should be such as it can be excreted by the kidneys Moreover, it can be used as linkers for peptides.

Still another example, collagen or collagen derivative can be used as a block by itself. In particular, collagen has a well known in-vivo history such as being biocompatible while being very strong mechanically. When using collagen as a middle block in the triblock protein polymer, at least two different forms of delivery are possible. First, the protein polymer can be delivered at about 10 to about 20% aqueous solution with an acidic pH at about 2 to about 5 and preferably between the range of about a pH of 3 to about a pH of 4. Temperature can range from 4° C. to 32° C. such as the solution can be delivered and the phase inversion occurs below body temperature. The natural pH of blood is slightly basic at about 7.35. When the acidic polymer delivered in vivo is coated along the arterial wall and over lesions, with or without a stent, the solution is in contact with blood. Accordingly, the pH of the protein polymer solution will increase and the polymer protein will gel as the polymer comes out of the solution and thus forming a gel or coating of film over the arterial wall and lesion, with or without a stent. Alternatively, the protein polymer can be delivered as a two component solution at about 10% aqueous solution of the polymer. The first component will be an acidic aqueous solution with a polymer concentration of about 10% to about 20% polymer. The other solution will be a basic buffered solution with a pH of greater than about 7. Upon mixing the two solutions in situ, the pH will increase and a gel forms as the polymer protein comes out of the solution and result in a coating on the arterial wall, the lesion and the deployed stent (if present).

All the embodiments of the triblock protein polymer described above in this application provide a biomimicry effect in that they possess chemical and mechanical properties biocompatible with the vascular environment in which the protein polymer is delivered. Also, all embodiments described in this application are inherently elastic and can further incorporate drugs, specific chemical structures and therapeutic agents to achieve a wide variety of different therapeutic effects. The unique viscoelastic property of the material, allowing it to stretch, elongate and store energy, comes from the elastin pentapeptide flanking blocks, the middle block to which they are attached, and their dynamic interaction. The middle block is designed to phase separate from the flanking blocks such that it can behave as an elastomeric material. It is also possible to attach drugs, amino acids, amino acid sequence, monomers, and other molecules to achieve additional benefits or therapeutic effects. "Attach" is defined as linked, coupled or otherwise attached as known in the art, including but not limited to molecular forces, physical size entrapment and chemical bonds. Alternatively these substances can be blended into the amorphous phase of the polymer material and released in a controlled fashion through diffusion. Thus the drugs or any therapeutic agents incorporated or attached to the middle block are delivered as part of the polymer solution to the target region in a vessel.

In other words, drugs such as everolimus, sirolimus, paclitaxel, clobetasol etc., can be transported by the protein elastin-based polymer in at least two different ways. First, the drug can be incorporated as part of the triblock structure, where the drug will be released upon phase separation from the flanking blocks when the covalent bonds attaching the middle block to the polymer backbone are broken. Second, the drug can be dissolved into the polymer matrix and become physically trapped inside the structure of the polymer. In this case, the drug can be released by erosion or diffusion. Erosion occurs when the polymer itself degrades. As the polymer degrades over time, the trapped drug will be slowly released. Alternatively, diffusion may take place by simply having the drug diffuses outward from the polymer based upon concentration gradient, or water can diffuse into the structure of the polymer, dissolving the drug, and then having the dissolved drug diffusing out of the polymer structure. The first method of drug transportation via incorporation as a middle block is less commonly because covalent bonds are more difficult to break while the latter method of drug transportation via dissolving into the polymer matrix is more commonly used because that material is easier to prepare and have less regulatory issues.

With the various chemical compositions described herein, reinforcement of the vulnerable plaque is possible by using the inherent viscoelastic properties of the protein polymer. Furthermore, a pro-healing effect can be accomplished by promoting proliferation and migration of endothelial cells, with or without a stent, or by delivering drugs with a controlled release, with or without a stent. More importantly, by smearing or coating the artery with a particular chemical composition, a protein polymer may promote healing of the artery by removing lipid from plaque using the coating and the drugs contained within.

In one example, specific peptide sequences such as (argenine-glysine-aspartic acid) RGD or other endothelial cell specific sequences such as serine-isoleucine-lysine-alanine-valine (SIKAV) [SEQ ID NO. 7], A-, B-, and C-natriuretic peptide, and (argenine-glycine-aspartic acid-tyrosine-isoleucine-glycine-serine-argenine-glycine) YIGSRG [SEQ ID NO. 8] can be attached to the amino acids in the middle block component or as a separate middle block component or as a middle block by itself. These sequences are accessible to cells and proteins, and are found at the surface of the polymer. While they can be part of the main chain, it is preferable they be attached to the main chain through a linker such as PEG, alkyl chain or other commonly used linkers known in the art. The peptide sequences trigger cellular mechanisms involved in cellular proliferation and migration, such as attachment, by binding to proteins on the cell surface. They show different levels of efficacy and specificity towards effecting endothelial cells, smooth muscle cells, platelets or proteins. The effect of these peptides has been shown in-vitro or in-vivo. Their position in the triblock will only influence the accessibility of peptide. These peptide sequences are active compounds. They promote endothelial cells proliferation and migration, thus indirectly promote healing in the artery once the peptide sequences are delivered to the targeted vessel region along with the polymer solution after it is attached to or incorporated as part of the middle block component of the polymer.

In another example, another peptide sequence, RAD16-II, is used. This sequence has the structure "—AcNRARADA-DARARADADA-CNH$_2$" [SEQ ID NO. 9], where R, A, D are the standard amino acids arginine, alanine, and aspartic acid respectively, and Ac indicates acetylation. This particular peptide sequence has the characteristics of aiding cell entrapment and viability or as a restraining depot to house nano or microparticles/fibers. Thus, it prevents wash out of the trapped or stored molecules and can be used to incorporate and deliver elutable drugs, peptides or proteins. Consequently, when combined with and attached to the triblock protein polymer middle block, this peptide sequence can give the protein polymer an added benefit of delivering drug in a controlled release fashion. This peptide forms a solution at a low pH and osmolarity, yet forms a gel at a physiological pH and osmolarity. Therefore, a triblock protein polymer with the RAD16-II peptide sequence can be delivered in two forms. First as a low concentration aqueous solution of about 10% polymer protein with an acidic pH so that the when in contact with blood in situ where the basic pH is greater than about 7 the mixing will cause gelation. Alternatively, the peptide sequence incorporated into the triblock protein polymer can be delivered as a two component solution where a first solution at about 5% to about 25% protein polymer aqueous solution at low osmolarity with an acidic pH is mixed with second solution containing a solution of salts such as sodium chloride (NaCl), where mixing of the two solutions in situ will result in gelation. Furthermore, other assembled peptides that can also be used in place of RAD-16 include, but are not intended to be limited to, MAX-1 with the sequence "VKVKVKVKV-PP-TKVKVKVKV-NH$_2$" [SEQ ID NO. 10] and EAK16-II with the sequence "AcN-AEAEAKA-KAEAEAKAK-CNH$_2$" [SEQ ID NO. 11].

The peptide apolipoprotein-A1 (ApoA1) can be used to enhance the transport of lipids back into the blood flow. This peptide can be encapsulated in a micelle, liposome, microparticle or nano-particle, and the like particles, for protection and/or sustained controlled delivery and transport into the cell. These particles can be delivered through one of the gel components and can be embedded in the gel. The peptide is to diffuse into the cells in the plaque to bind to lipids and transport them back into the bloodstream by reverse cholesterol transport. Therefore Apo-A1, the therapeutic agent is embedded into the polymer and delivered to the target region as part of the solution. They are suitable for treating regions with a stenosis or diffuse disease but untreated by conventional percutaneous treatments.

Alternatively, besides applying directly into the artery wall and lesions in the form of a solution as described in all the above embodiments, the triblock protein polymer may be coated onto stents with or without other coatings. Using the most basic form of the triblock protein polymer, [(VPGVG)$_4$(VPGLG)$_n$(VPGVG)$_4$]$_m$ [SEQ ID NO. 3] or a variation of another hydrophilic middle block replacing "L", lysine, with another hydrophilic amino acid such as arginine, aspartic acid, or glutamic acid, simply as a top coat, a stent with the triblock protein is expected to provide a biocompatible interface between the stent and the arterial wall, potentially promoting re-endothelialization and thus improve healing response of the vessel after stenting. Other variations such as attachment of the RAD16-II peptide sequence to the middle block will allow the polymer to store or retain drugs such as everolimus, sirolimus, paclitaxel, and a cyclic peptide containing a RGD sequence known as c-RGD (cyclic-ROD). Similarly, other linear ROD as well as RGD peptide mimetics, i.e., drugs designed to mimic the shape, polarity conformation of the peptide, can also be used. In this embodiment, the triblock polymer protein coating not only contains a biomimicry effect to give a more biocompatible environment, but also act as a drug release control layer to deliver drug deposited into the coating in a controllable fashion.

In this embodiment, incorporating RGD or specific endothelial cells specific sequences such as SIKVAV [SEQ ID NO. 7], CNP, and YIGSRG [SEQ ID NO. 8] into a triblock protein polymer coated onto a stent can be used to promote re-endothelialization of the vessel after the stent is delivered and deployed. This will give the operator physician an opportunity to deliver a solution of triblock polymer protein with a different therapeutic effect such as drug delivery thus generating a complimentary effect to stenting. Therefore, as described, the triblock polymer protein can be used as a coating on the stent as well as an independently delivered solution. When used to coat a stent, the polymer protein will be dissolved in water (at about 1% to about 10% wt polymer) or organic solvent such as tetrahydrofuran (THF), and spray coated onto stents with or without other coatings. Other methods of coating a stent such as dip coating, hand coating or painting the stents can also be used. This polymer may also contain other drugs such as everolimus, sirolimus, paclitaxel, and clobetasol, etc.

Now various modes of delivering the triblock protein polymer into the artery to the target lesion arterial walls with or without the combination with a stent will be described. It should be noted that variations of drug coatings can be used on stents in combination with the triblock protein polymer delivered. One skilled in the art can naturally complement the independent effects of stenting, drug coating on the stent, and the supplemental triblock protein polymer coating with each other. Furthermore, the catheter can be made of a thermoelectric material that can keep the polymer solution cool while the polymer is in the body to prevent gelation by conduction of electricity. In the case where two solutions are used for mixing to form a coating, a delivery system capable of delivering two solution substantially simultaneously such as a dual lumen catheter where mixing occur only outside the delivery balloon can be used.

Figure 7:
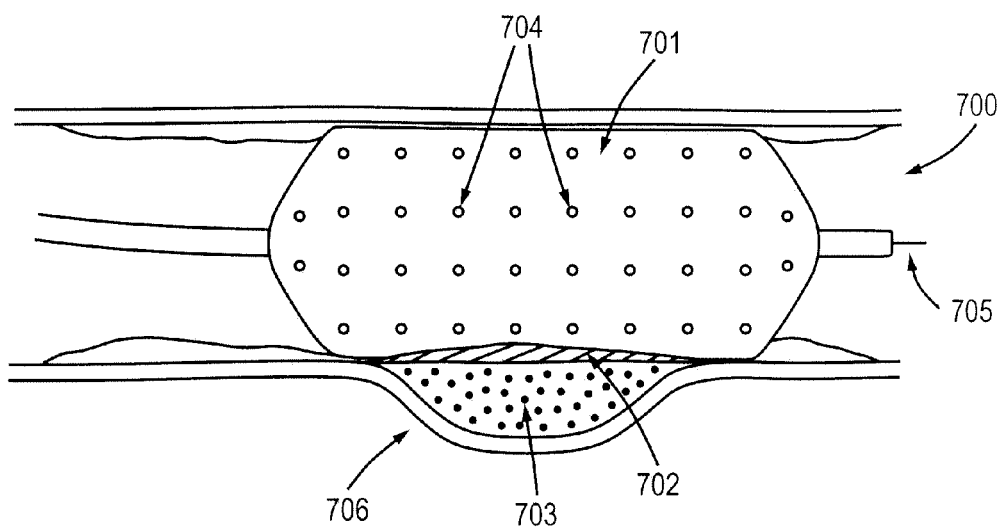
FIG. 7 illustrates the use of a porous balloon to deliver a triblock polymer protein to a vulnerable plaque lesion.

FIG. 7 illustrates a mode of delivering a triblock protein polymer solution to the target site in a diseased artery. FIG. 7 shows the use of a porous balloon 701 to deliver a triblock polymer protein to one of many possible lesion in a region of the artery such as a vulnerable plaque lesion 706. A vulnerable plaque 906 with a fibrous cap 702 and a lipid core 703 is located in an artery. The porous balloon is delivered into the arterial lumen 700 with the assistance of a guide wire 705 and expanded. There are many pores 704 on the surface of the balloon 701. A benefit of using a porous balloon is such that the amount of triblock protein polymer delivered onto the arterial wall can be evenly distributed because of the spacing of the pores. Further, the porous balloon 701 cannot be over pressurized and thus minimizing injury to the blood vessel. To assure even distribution of the triblock protein polymer solution along the vessel wall and over the vulnerable plaque, the porous balloon can be repositioned distally, proximally and radially about its center to ensure even distribution on the vessel wall. Moreover, for the form of the polymer compound that is temperature sensitive, the catheter will be constructed to prevent the polymer from warming up by the blood. This can be accomplished by a hollow wall catheter design, special insulation materials, and even a layer of cooling material in the hollow wall to prevent temperature increase. Moreover, the catheter can be made of a thermoelectric material that can keep the polymer solution cool while the polymer is in the body to prevent gelation by conduction of electricity. In the case where two solutions are used for mixing to form a coating, a delivery system capable of delivering two solution substantially simultaneously such as a dual lumen catheter where mixing occur only outside the delivery balloon can be used.

Figure 8A:
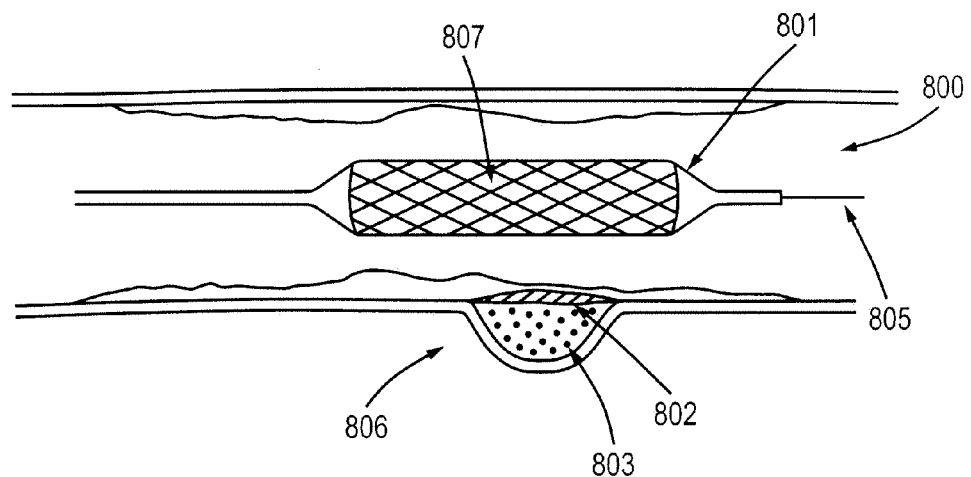
FIG. 8A illustrates a crimped stent mounted over a balloon guided by a guide wire delivered into an arterial lumen with a vulnerable plaque lesion having a fibrous cap and a lipid core.
Figure 8B:
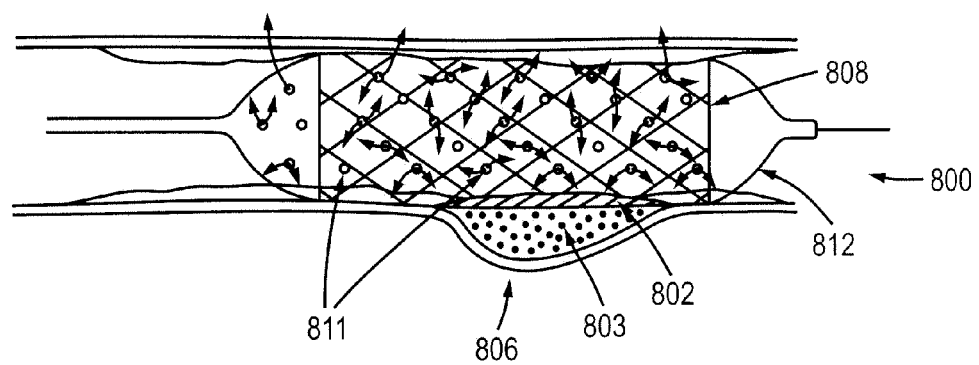
FIG. 8B illustrates a stent expanded against the vessel wall and the fibrous cap.

FIGS. 8A and 8B illustrate delivery of the triblock protein polymer solution as an adjunctive therapy after stenting. FIG. 8A shows a crimped stent 807 mounted over a balloon guided by a guide wire 805 and delivered into an arterial lumen 800 with a vulnerable plaque lesion 806 having a fibrous cap 802 and lipid core 803. FIG. 8B shows the same arterial lumen with the stent 808 expanded against the vessel wall and the fibrous cap 802 to provide support inside the arterial lumen. The stent 808 may or may not have a coating. After the stent 808 is delivered, either the stent delivery balloon is withdrawn and a porous balloon 812 with pores 811 is advanced to the site to deliver the triblock polymer protein solution, or, the porous balloon 812 itself may be used to delivery the stent 808. As would be understood by one skilled in the art, the balloon may be oversized, or that another non-porous balloon may be utilized to ensure strut apposition to the wall if the stent is not well apposed against the lesion or other parts of the arterial wall because of plaque accumulation. In the case of a non-coated stent, the triblock protein polymer can serve as a coating to the lesion and the arterial wall to reinforce the fibrous cap of the vulnerable plaque and to provide a biocompatible environment to induce re-endothelialization. In the case where the stent is coated, the triblock protein polymer can perform the effect of reinforcing the fibrous cap in addition to providing another therapeutic effect such as drug delivery or promote healing, depending on the type of coating used on the stent. Similar to the embodiment previously described, the polymer delivery catheter will be specifically designed to insulate the polymer from temperature increase. This can be accomplished by a hollow wall catheter design, special insulation materials, and even a layer of cooling material in the hollow wall to prevent temperature increase.

Figure 9A:
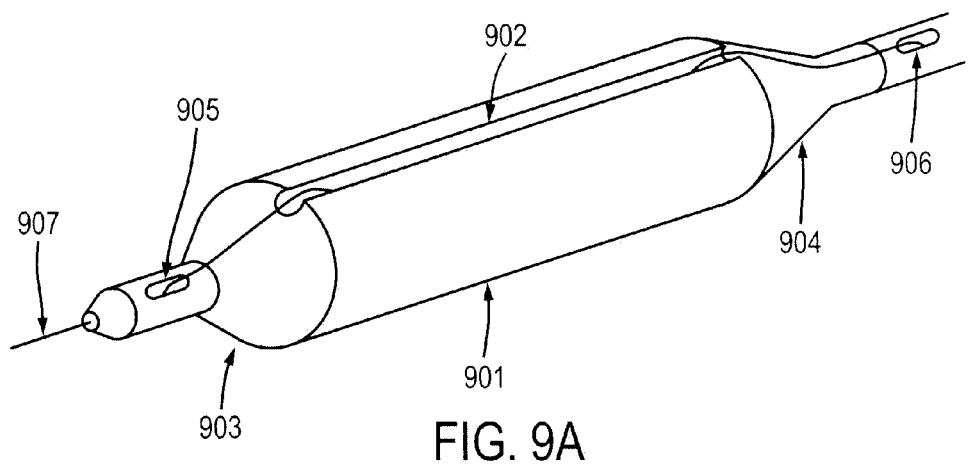
FIG. 9A illustrates a unique balloon with a groove on the outer profile of the balloon.
Figure 9B:
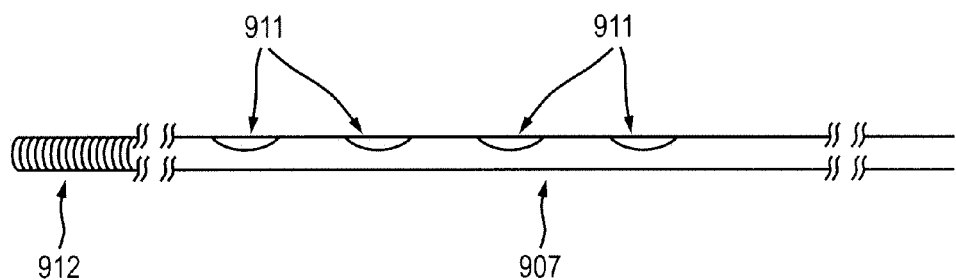
FIG. 9B illustrates a hollow guide wire with a floppy distal end and ports on the distal portion of the guide wire.

FIGS. 9A to 9D show yet another embodiment of delivering the triblock protein polymer in aqueous solution form to a target lesion inside an artery. FIG. 9A shows a unique balloon 901 with a groove 902 on the outer profile of the balloon once it is inflated. It has a distal shoulder 903 and a proximal shoulder 904 which may or may not have a groove that is continued from the main groove 902 on the outer profile of the balloon. The balloon has a wire port 906 in the proximal member and another wire port 905 in the distal member of the balloon for the guide wire 907. This unique balloon can be used with a hollow guide wire with ports in its distal end for delivery of the triblock protein polymer solution. FIG. 9B shows a hollow guide wire 907 with a floppy distal end 912 and ports 911 on the distal portion of the guide wire which are used to deliver solution when the ports are positioned in the groove along the outer profile of the balloon.

Figure 9C:
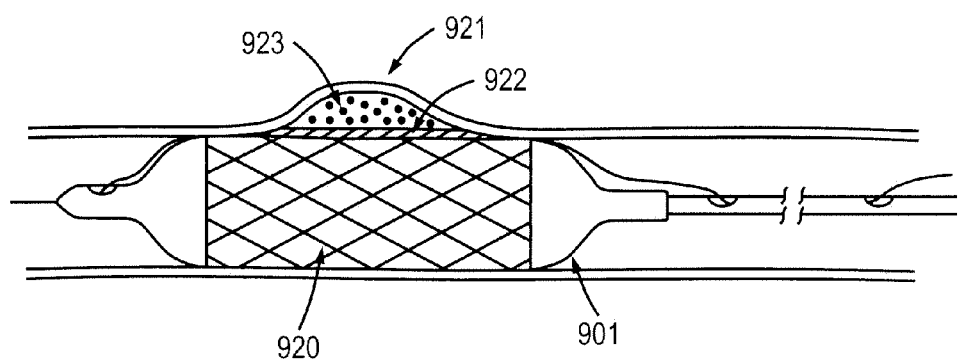
FIG. 9C illustrates an example of using the combination of a hollow guide wire and the uniquely shaped balloon to deploy a stent and deliver the triblock protein polymer solution.
Figure 9D:
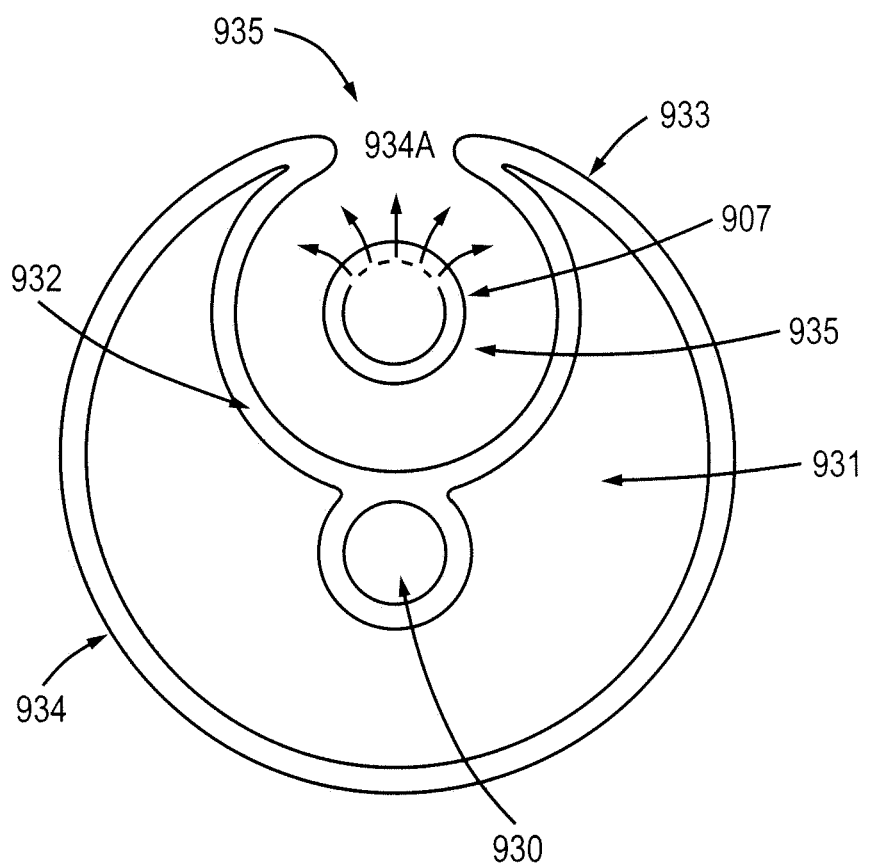
FIG. 9D illustrates a cross-sectional view of the hollow guide wire and the balloon.

FIG. 9D shows a cross-sectional view of the hollow guide wire and the balloon. As illustrated the balloon has a center inflation lumen 930 with varying thickness along the balloon wall. Wall portion 932 is the thickest followed by portion 933 which is thinner than 932 and portion 934 which is thinner than 933. The balloon groove creates a lumen or space 935 where the hollow guide wire 907 can move about. When the port holes along the distal end of the hollow guide wire are aligned to the groove opening 935, solution 934A can be delivered directly against the vessel wall to the lesion or target site.

FIG. 9C illustrates an example of using the combination of a hollow guide wire and the uniquely shaped balloon to deploy a stent and deliver the triblock protein polymer solution. As shown, the stent is originally mounted onto the uniquely shaped balloon and delivered with the assistance of the hollow guide wire to the target lesion such as, a vulnerable plaque 921 with a fibrous cap 922 and a lipid core 923. At the target site, the balloon is inflated and deployed. After the stent is well apposed against the lesion and the vessel wall, the guide wire is aligned with the groove opening and the triblock protein polymer solution can be delivered directly to the vulnerable plaque lesion. The advantage of this method of delivery is that the solution can be focused and delivered to a specific localized region only. In the case where an operator is trying to deliver the solution to the entire surface of the vessel wall in a segment of the vessel the operator can nevertheless still repeatedly rotate the balloon in a radial direction about the balloon's center axis to ensure coating of the vessel wall. Although repeated inflation of a previously known balloon may risk trauma to the vessel, leaving the balloon according to the present invention inflated will not cause any ischemic injury to the myocardial tissue because the groove permits blood to flow distally into the vessel. Similar to the embodiment previously described, the polymer delivery catheter will be specifically designed to insulate the polymer from temperature increase. This can be accomplished by a hollow wall catheter design, special insulation materials, and even a layer of cooling material in the hollow wall to prevent temperature increase. Further, the catheter can be made of a thermoelectric material that can keep the polymer solution cool while the polymer is in the body to prevent gelation by conduction of electricity. In the case where two solutions are used for mixing to form a coating, a delivery system capable of delivering two solution substantially simultaneously such as a dual lumen catheter where mixing occur only outside the delivery balloon can be used.

Figure 10A:
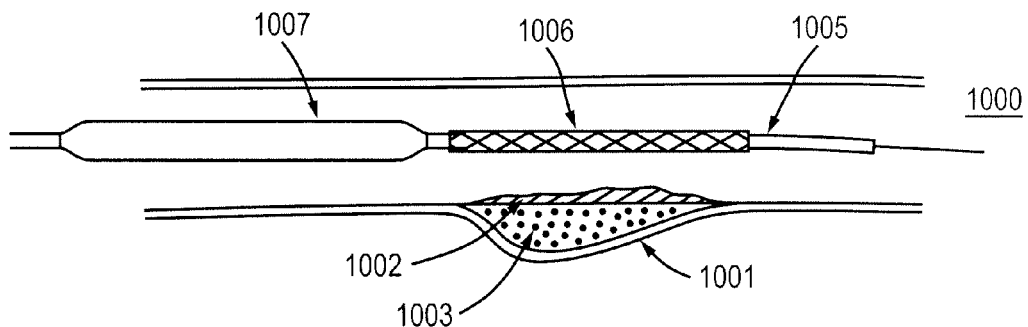
FIG. 10A illustrates a dual balloon catheter with a stent mounted over a non-porous balloon to deliver the protein polymer solution in a vessel with a vulnerable plaque having a fibrous cap and lipid core.
Figure 10B:
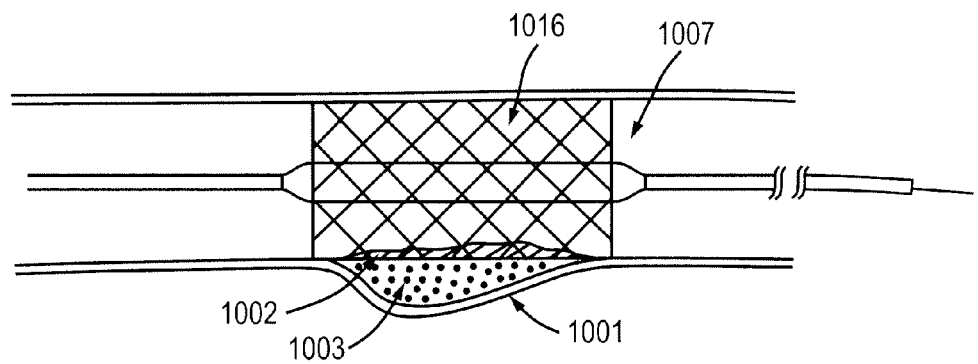
FIG. 10B illustrates a deployed stent at the vulnerable plaque with struts well apposed against the vessel wall and provide reinforcement to the fibrous cap.
Figure 10C:
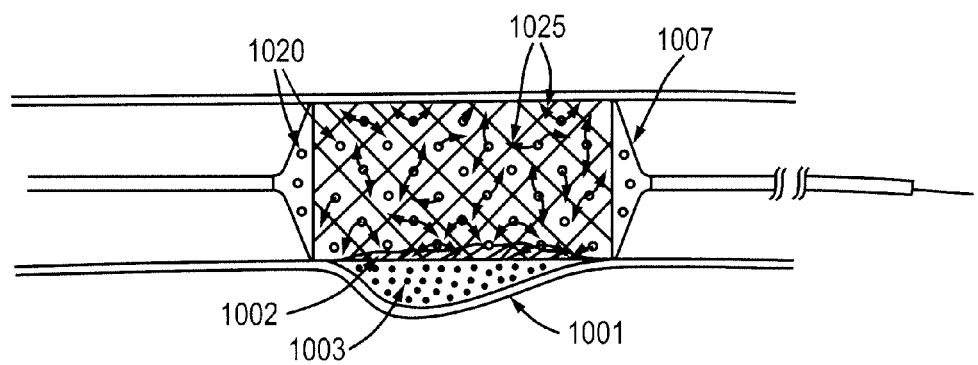
FIG. 10C illustrates the porous balloon expanded with pores dispersed along the outer surface of the balloon while the protein polymer is being delivered.

FIGS. 10A to 10C show yet another embodiment where a dual balloon catheter is used to deliver and deploy a stent as well as deliver a triblock protein polymer solution to the vessel. FIG. 10A shows a dual balloon catheter 1005 with a stent mounted over a non-porous balloon 1006 distal to a porous balloon 1007 used to deliver the protein polymer solution in a vessel with a vulnerable plaque 1001 having a fibrous cap 1002 and lipid core 1003. FIG. 10B shows a deployed stent 1016 at the vulnerable plaque 1001 with struts well apposed against the vessel wall and provide reinforcement to the fibrous cap 1002. In this figure, the non-porous balloon (not shown) is distal to the porous balloon 1007 which is still unexpanded but positioned within the deployed stent. FIG. 10C shows that the porous balloon 1007 has been expanded with pores 1020 dispersed along the outer surface of the balloon while the protein polymer is being delivered 1025 to coat the vessel wall and the fibrous cap 1002 of the vulnerable plaque lesion. As would be understood by one skilled in the art that the configuration of this dual balloon catheter can be easily modified. For example, the stent delivery balloon can be placed proximal to the porous solution delivery balloon. Similarly, rather than using a balloon inflatable stent, a self expanding stent can be used instead. In this case, there only need to have one balloon, that of the porous solution delivery balloon. In the case of a self expanding stent, it is likely that the self expanding stent will be positioned proximal to the porous solution delivery balloon where the sheath can be retracted proximally without impinging on the balloon inflation. Similar to the embodiment previously described, the polymer delivery catheter will be specifically designed to insulate the polymer from temperature increase. This can be accomplished by a hollow wall catheter design, special insulation materials, and even a layer of cooling material in the hollow wall to prevent temperature increase. Further, the catheter can be made of a thermoelectric material that can keep the polymer solution cool while the polymer is in the body to prevent gelation by conduction of electricity. In the case where two solutions are used for mixing to form a coating, a delivery system capable of delivering two solution substantially simultaneously such as a dual lumen catheter where mixing occur only outside the delivery balloon can be used.

Figure 11A:
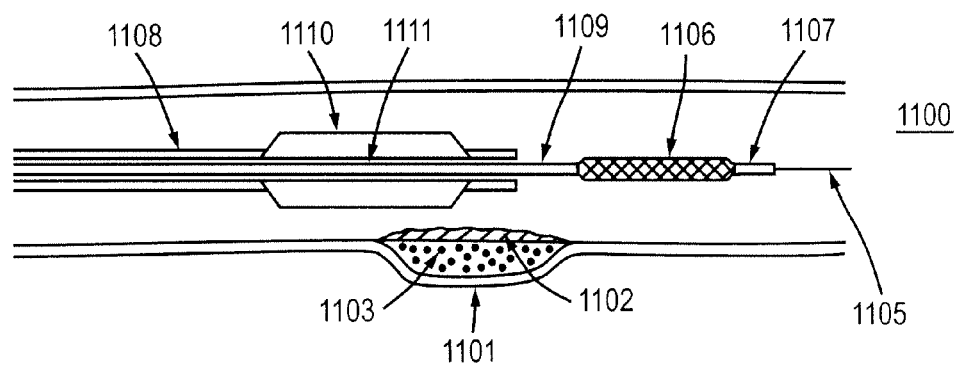
FIG. 11A illustrates a vulnerable plaque lesion within a vessel lumen containing a lipid core covered by a fibrous cap.
Figure 11B:
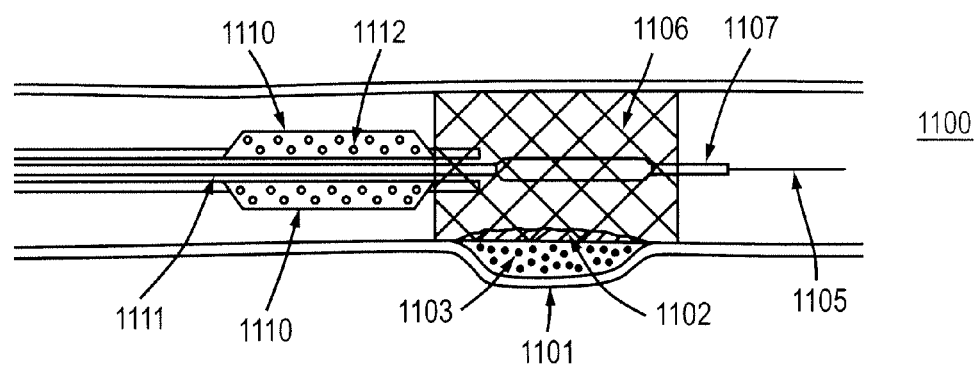
FIG. 11B illustrates a stent deployed at the target site with the stent struts well apposed against the vessel wall including the vulnerable plaque lesion, providing reinforcement and support to the fibrous cap.
Figure 11C:
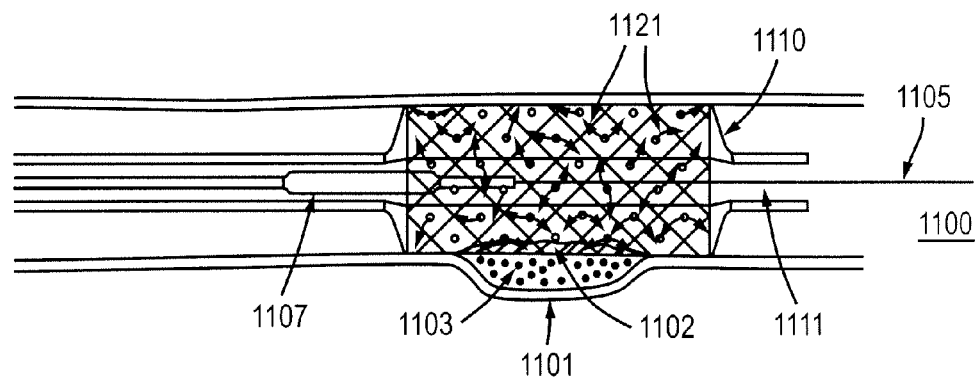
FIG. 11C illustrates the inflation of the porous balloon at the stent deployment site and deliver of agents over the vulnerable plaque lesion.

FIGS. 11A to 11C show another embodiment of a combination device including a stent delivery catheter housed within a porous balloon catheter to deliver and deploy a stent in addition to delivering the triblock protein polymer solution using the porous balloon. FIG. 11A illustrates a vulnerable plaque lesion 1101 within a vessel lumen 1100 containing a lipid core 1103 covered by a fibrous cap 1102. A stent 1106 is mounted on a stent delivery catheter 1107 which is guided into the vessel lumen 1100 by a guide wire 1105. In fact, as shown in FIGS. 11A to 11C, this entire stent delivery system is housed within a catheter lumen 1111 of a porous balloon catheter body 1108. Although an inflatable balloon is illustrated in FIG. 11A, it is understood by those skilled in the art that this system can easily be replaced with a self-expanding stent system. In this therapy, treatment is to first deliver and deploy the stent at the target site or lesion of the vessel. FIG. 11B illustrates a stent 1106 deployed at the target site with the stent struts well apposed against the vessel wall including the vulnerable plaque lesion, providing reinforcement and support to the fibrous cap 1102. This figure also shows that the deflated balloon and catheter is retracted back to within the porous balloon catheter lumen 1111, while the porous balloon 1110 with pores 1112 is being advanced distally towards the target site lesion. FIG. 11C shows the inflation of the porous balloon 1110 at the stent deployment site and thus directly over the vulnerable plaque lesion 1101 and the fibrous cap 1102. As the balloon 1110 is inflated, so too is the triblock protein polymer 1121 is forced out of the pores 1112 to thereby coat the vessel wall. The stent delivery catheter 1107 of FIG. 11C is shown entirely retracted within the lumen of the porous balloon catheter while the guide wire 1105 remains in position. The porous balloon 1110 and its catheter body 1108 can be advanced distally or retracted proximally to deliver the triblock protein polymer solution to coat portions of the vessel wall which are distal and proximal to the target lesion site. Similar to the embodiment previously described, the polymer delivery catheter will be specifically designed to insulate the polymer from temperature increase. This can be accomplished by a hollow wall catheter design, special insulation materials, and even a layer of cooling material in the hollow wall to prevent temperature increase.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A method to treat a vessel comprising:
   identifying a target region in a vessel comprising an artery;
   delivering a protein elastin-based polymer solution to the target region in the vessel using a delivery system, the delivery system comprising a catheter and a porous balloon; and
   coating the target region with the protein elastin-based polymer solution, wherein the porous balloon evenly distributes the solution onto walls of the artery, and wherein the porous balloon includes pores along the entire length of the porous balloon that touches the walls of the artery.

2. The method of claim 1 wherein an area in the vessel adjacent to the target region of the vessel is also coated with the protein elastin-based polymer.

3. The method of claim 1 wherein the protein elastin-based polymer forms an elastic coating on the vessel wall after the vessel wall is coated with the protein elastin-based polymer solution.

4. The method of claim 3 wherein the elastic coating has a property that stabilizes the target region.

5. The method of claim 3 wherein the elastic coating has a property that reinforces the target region.

6. The method of claim 3 wherein the elastic coating has a property that protects the target region.

7. The method of claim 3 wherein the elastic coating further comprises a treatment agent.

8. The method of claim 7 wherein the elastic coating is capable of controlled release of the treatment agent for absorption by the vessel.

9. The method of claim 1 wherein the protein elastin-based polymer further comprises triblock structure consisting of two flanking blocks and a middle block wherein each block further comprises at least one component.

10. The method of claim 9 wherein a component within each block within the triblock structure is selected from a group consisting of an amino acid, an amino acid sequence or a monomer.

11. The method of claim 9 wherein the triblock structure further comprises an elastin pentapeptide as a flanking block to provide a viscoelastic property.

12. The method of claim 9 wherein a variant elastin pentapeptide of the flanking block is used as a middle block to provide backbone support.

13. The method of claim 9 wherein a variant elastin pentapeptide of the flanking block is used as a middle block to provide biocompatibility.

14. The method of claim 9 wherein a variant elastin pentapeptide of the flanking block is used as a middle block to provide a drug delivery property.

15. A method to treat a vessel comprising:
identifying a target region in a vessel comprising an artery;
delivering a protein elastin-based polymer solution to the target region in the vessel using a delivery system, the delivery system comprising a catheter and a porous balloon, wherein the porous balloon includes pores along the entire length of the porous balloon that touches an inner wall of the artery; and
coating the target region with the protein elastin-based polymer solution, wherein the protein elastin-based polymer further comprises triblock structure consisting of two flanking blocks and a middle block wherein each block further comprises at least one component, and wherein the protein triblock structure is of the general formula $(VPGVG)_4(VPGXG_n(VPGVG)_4)$, wherein X is selected from the group consisting of Lysine [SEQ ID NO. 60], arginine [SEQ ID NO. 12], glutamic acid [SEQ ID NO. 13], and aspartic acid [SEQ ID NO. 14].

16. The method of claim 10 wherein one or more pendant groups are attached to at least one component of the protein triblock structure.

17. The method of claim 16 wherein the pendant group is selected from a group consisting of phosphorylcholine (PC) and polyethylene glycol (PEG).

18. The method of claim 17 to reinforce a fibrous cap and increase reendothelialization of vessel arterial lining.

19. The method of claim 16 wherein the pendant group is selected from the group consisting of an acrylate, vinyl sulfones, vinyl ethers, allyl ethers, maleimides, and activated esters.

20. The method of claim 16 wherein the pendant group is attached to the middle block.

21. The method of claim 20 wherein the pendant group is selected from the group consisting of sulfonic acids, sulfonic salts, sulfonates, amines and amides.

22. The method of claim 20 wherein the pendant group is a peptide sequence.

23. The method of claim 9 wherein a peptide sequence acts as the middle block by itself.

24. The method of claim 22 or 23 wherein the peptide sequence is RAD16-II.

25. The method of claim 22 or 23 wherein the peptide sequence is RGD.

26. The method of claim 22 or 23 wherein the peptide sequence is SIKAV [SEQ ID NO. 7].

27. The method of claim 22 or 23 wherein the peptide sequence is YIGSRG [SEQ ID NO. 8].

28. A method to treat a vessel comprising:
identifying a target region in a vessel comprising an artery;
delivering a protein elastin-based polymer solution to the target region in the vessel using a delivery system, the delivery system comprising a catheter and a porous balloon, wherein the porous balloon includes pores along the entire length of the porous balloon that touches an inner wall of the artery; and
coating the target region with the protein elastin-based polymer solution, wherein the protein elastin-based polymer further comprises triblock structure consisting of two flanking blocks and a middle block wherein each block further comprises at least one component, and wherein the triblock protein polymer is of the general formula $(VPGVG)_4(X)$ [SEQ ID NOS. 4-5], where X is selected from a group consisting of polyethylene glycol (PEG), poly(hydroxyethyl methacrylate) (polyHEMA), poly(vinyl pyrrolidinone) (PVP), and collagen.

29. The method of claim 9 wherein the protein triblock polymer is delivered below the LCST of the polymer to form a coating on the vessel wall.

30. The method of claim 9 wherein the protein triblock polymer comprises a two component solution.

31. The method of claim 30 wherein a first component is a triblock polymer and a second component comprises a cross-linking compound that are mixed in situ to result in a coating on the vessel wall.

32. The method of claim 31 wherein the first component and the second component of the two component solution are delivered substantially simultaneously.

33. The method of claim 31 wherein the cross-linking compound is a di- or poly-thiol functionalized compound.

34. The method of claim 30 wherein a second component solution is of a different pH than the first component solution.

35. The method of claim 30 wherein a second component solution is of an osmolarity different than that of the first component solution.

36. The method of claim 7 wherein the treatment agent further comprises at least one of a member selected from the group consisting of agents which promote endothelialization, agents which promote healing, and agents which remove lipid from plaque.

37. The method of claim 1 wherein the target region further comprises at least one of a denuded endothelial region, a stenotic region treated or not treated for stenosis, an inflamed vessel segment, a region anticipated to be stenotic or inflammatory, and a region with a vulnerable plaque.

38. The method of claim 37 wherein the protein elastin-based polymer reinforces and stabilizes the fibrous cap of a vulnerable plaque to prevent rupture of the fibrous cap.

39. The method of claim 1 wherein the delivery system comprises an inflatable balloon catheter wherein the protein elastin-based polymer is delivered by inflating the porous balloon at the target lesion.

40. The method of claim 39 wherein inflatable balloon is a complementary therapy to a drug eluting stent.

41. The method of claim 1 wherein the protein elastin-based polymer inside the delivery system is at a temperature that is below the temperature of the blood outside the delivery catheter system.

42. The method of claim 41 wherein the delivery system is made of a thermoelectric material or an insulating material.

43. The method of claim 1, wherein delivering a solution comprises delivering at a temperature between 1° C. and 10° C.

44. The method of claim 1, wherein the protein elastin-based polymer solution comprises a ten percent aqueous solution.

45. A method to treat a vessel comprising:
identifying a target region in a vessel;
delivering a protein elastin-based polymer solution to the target region in the vessel using a delivery system, wherein the delivery system comprises a porous balloon that includes pores along the entire length of the porous balloon that touches an inner wall of the artery, wherein the protein elastin-based polymer solution comprises a protein elastin-based polymer comprising a triblock structure including two flanking blocks and a middle block wherein a component within each block is selected from the group consisting of an amino acid, an amino acid sequence and a monomer and the middle block comprises a pendant group comprising a peptide sequence of YIGSRG [SEQ ID NO. 8]; and
coating the target region with the protein elastin-based polymer solution.

46. A method to treat a vessel comprising:
identifying a target region in a vessel;
delivering a protein elastin-based polymer solution to the target region in the vessel using a delivery system, wherein the delivery system comprises a porous balloon that includes pores along the entire length of the porous balloon that touches an inner wall of the artery, wherein the protein elastin-based polymer solution comprises a protein elastin-based polymer comprises a triblock structure including two flanking blocks and a middle block wherein a component within each flanking block is selected from the group consisting of an amino acid, an amino acid sequence and a monomer and the middle block comprises a peptide sequence of YIGSRG [SEQ ID NO. 8]; and
coating the target region with the protein elastin-based polymer solution.

47. The method of claim 1, further comprising delivering the protein elastin-based polymer solution to a vessel comprising an artery to repair the artery.

48. A method to treat a vessel comprising:
identifying a target region in a vessel comprising an artery;
delivering a protein elastin-based polymer solution to the target region in the vessel using a delivery system, the delivery system comprising a catheter and a porous balloon; and
coating the target region with the protein elastin-based polymer solution, wherein the porous balloon forces the solution evenly into, and protectively coats the entire surface of a length and circumference of the inner wall of the artery, and wherein the porous balloon includes pores along the entire length of the porous balloon that touches the inner wall of the artery.

49. The method of claim 48, further comprising delivering the protein elastin-based polymer to a vessel comprising an artery to repair the artery.

50. A method to treat a vessel comprising:
identifying a target region in a vessel comprising an artery;
delivering a protein elastin-based polymer solution to the target region in the vessel using a delivery system, the delivery system comprising a catheter and a porous balloon; and
coating the target region with the protein elastin-based polymer solution, wherein the porous balloon forces the solution evenly into, and protectively coats the entire surface of a length and circumference of the inner wall of the artery, wherein the porous balloon is rotated while forcing the solution evenly into the length and circumference, in order to protectively coat the entire surface of the length and circumference.

* * * * *

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 1

Val Pro Gly Leu Gly
1               5

```
<210> SEQ ID NO 2
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 2

Val Pro Gly Val Gly
1               5

<210> SEQ ID NO 3
<211> LENGTH: 45
<212> TYPE: PRT
<213> ORGANISM: Artificial Sequence
<220> FEATURE:
<223> OTHER INFORMATION: Synthetic peptide sequence

<400> SEQUENCE: 3

Val Pro Gly Val Gly Val Pro Gly Val Gly Val Pro Gly Val Gly Val
1               5                   10                  15

Pro Gly Val Gly Val Pro Gly Leu Gly Val Pro Gly Val Gly Val Pro
            20                  25                  30

Gly Val Gly Val Pro Gly Val Gly Val Pro Gly Val Gly
        35                  40                  45

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<223> OTHER INFORMATION: Initial 20 amino acids (1-20) of the polymer
      backbone of Figure 6

<400> SEQUENCE: 4

Val Pro Gly Val Gly Val Pro Gly Val Gly Val Pro Gly Val Gly Val
1               5                   10                  15

Pro Gly Val Gly
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<223> OTHER INFORMATION: Terminal 20 amino acids (21-40) of the polymer
      backbone of Figure
      6

<400> SEQUENCE: 5

Val Pro Gly Val Gly Val Pro Gly Val Gly Val Pro Gly Val Gly Val
1               5                   10                  15

Pro Gly Val Gly
            20

<210> SEQ ID NO 6
<211> LENGTH: 45
<212> TYPE: PRT
<213> ORGANISM: Artificial Sequence
<220> FEATURE:
<223> OTHER INFORMATION: Synthetic peptide sequence
```

```
<400> SEQUENCE: 6

Val Pro Gly Val Gly Val Pro Gly Val Gly Val Pro Gly Val Gly Val
1               5                   10                  15

Pro Gly Val Gly Val Pro Gly Lys Gly Val Pro Gly Val Gly Val Pro
                20                  25                  30

Gly Val Gly Val Pro Gly Val Gly Val Pro Gly Val Gly
                35                  40              45

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 7

Ser Ile Lys Ala Val
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 8

Arg Gly Asp Tyr Ile Gly Ser Arg Gly
1               5

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide sequence

<400> SEQUENCE: 9

Arg Ala Arg Ala Asp Ala Asp Ala Arg Ala Arg Ala Asp Ala Asp Ala
1               5                   10                  15

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide sequence

<400> SEQUENCE: 10

Val Lys Val Lys Val Lys Val Lys Val Pro Pro Thr Lys Val Lys Val
1               5                   10                  15

Lys Val Lys Val
                20

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide sequence

<400> SEQUENCE: 11

Ala Glu Ala Glu Ala Lys Ala Lys Ala Glu Ala Glu Ala Lys Ala Lys
1               5                   10                  15
```

-continued

```
<210> SEQ ID NO 12
<211> LENGTH: 45
<212> TYPE: PRT
<213> ORGANISM: Artificial Sequence
<220> FEATURE:
<223> OTHER INFORMATION: Synthetic peptide sequence

<400> SEQUENCE: 12

Val Pro Gly Val Gly Val Pro Gly Val Gly Val Pro Gly Val Gly Val
1               5                   10                  15

Pro Gly Val Gly Val Pro Gly Arg Gly Val Pro Gly Val Gly Val Pro
            20                  25                  30

Gly Val Gly Val Pro Gly Val Gly Val Pro Gly Val Gly
        35                  40                  45

<210> SEQ ID NO 13
<211> LENGTH: 45
<212> TYPE: PRT
<213> ORGANISM: Artificial Sequence
<220> FEATURE:
<223> OTHER INFORMATION: Synthetic peptide sequence

<400> SEQUENCE: 13

Val Pro Gly Val Gly Val Pro Gly Val Gly Val Pro Gly Val Gly Val
1               5                   10                  15

Pro Gly Val Gly Val Pro Gly Glu Gly Val Pro Gly Val Gly Val Pro
            20                  25                  30

Gly Val Gly Val Pro Gly Val Gly Val Pro Gly Val Gly
        35                  40                  45

<210> SEQ ID NO 14
<211> LENGTH: 45
<212> TYPE: PRT
<213> ORGANISM: Artificial Sequence
<220> FEATURE:
<223> OTHER INFORMATION: Synthetic peptide sequence

<400> SEQUENCE: 14

Val Pro Gly Val Gly Val Pro Gly Val Gly Val Pro Gly Val Gly Val
1               5                   10                  15

Pro Gly Val Gly Val Pro Gly Asp Gly Val Pro Gly Val Gly Val Pro
            20                  25                  30

Gly Val Gly Val Pro Gly Val Gly Val Pro Gly Val Gly
        35                  40                  45
```